US012649056B2

(12) United States Patent
Schmidt et al.

(10) Patent No.: US 12,649,056 B2
(45) Date of Patent: Jun. 9, 2026

(54) MEDICAL DEVICES FOR TREATMENT OF CANCER WITH ELECTRIC FIELDS

(71) Applicant: Cardiac Pacemakers, Inc., St. Paul, MN (US)

(72) Inventors: Brian L. Schmidt, White Bear Lake, MN (US); Jacob M. Ludwig, Isanti, MN (US); Benjamin J. Haasl, Forest Lake, MN (US); Michael J. Kane, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/166,957

(22) Filed: Oct. 22, 2018

(65) Prior Publication Data

US 2019/0117969 A1     Apr. 25, 2019

Related U.S. Application Data

(60) Provisional application No. 62/575,681, filed on Oct. 23, 2017.

(51) Int. Cl.
  A61N 1/36       (2006.01)
  A61N 1/04       (2006.01)
      (Continued)

(52) U.S. Cl.
  CPC ........ A61N 1/36002 (2017.08); A61N 1/0408 (2013.01); A61N 1/0424 (2013.01);
      (Continued)

(58) Field of Classification Search
  CPC .... A61N 1/36002; A61N 1/0408; A61N 1/32; A61N 1/06; A61N 1/37247; A61N 1/05;
      (Continued)

(56) References Cited

U.S. PATENT DOCUMENTS

| | | | |
|---|---|---|---|
| 4,016,886 A | 4/1977 | Doss et al. | |
| 4,369,791 A | 1/1983 | Friedman | |

(Continued)

FOREIGN PATENT DOCUMENTS

| | | | |
|---|---|---|---|
| AU | 2005301103 | 5/2006 | |
| CN | 1561925 | 1/2005 | |

(Continued)

OTHER PUBLICATIONS

Giladi, M., Schneiderman, R., Voloshin, T. et al. Mitotic Spindle Disruption by Alternating Electric Fields Leads to Improper Chromosome Segregation and Mitotic Catastrophe in Cancer Cells. Sci Rep 5, 18046 (2016) (Year: 2016).*

(Continued)

*Primary Examiner* — Erica S Lee
(74) *Attorney, Agent, or Firm* — Pauly, DeVries Smith & Deffner LLC

(57)               ABSTRACT

Embodiments herein include medical devices and methods for using the same to treat cancerous tumors within a bodily tissue. In an embodiment, a medical device is included. The medical device can include an electric field generating circuit configured to generate one or more electric fields and control circuitry in communication with the electric field generating circuit. The control circuitry can be configured to control the generation of one or more electric fields from the electric field generating circuit. The control circuitry can cause the electric field generating circuit to deliver one or more electric fields at one or more frequencies selected from a range of between 10 kHz to 1 MHz to a cancerous tumor located within a bodily tissue. Other embodiments are also included herein.

9 Claims, 13 Drawing Sheets

(51) Int. Cl.
    *A61N 1/05*       (2006.01)
    *A61N 1/06*       (2006.01)
    *A61N 1/32*       (2006.01)
    *A61N 1/372*      (2006.01)

(52) U.S. Cl.
    CPC ................ *A61N 1/05* (2013.01); *A61N 1/06*
        (2013.01); *A61N 1/32* (2013.01); *A61N*
        *1/37247* (2013.01); *A61N 1/36031* (2017.08);
        *A61N 1/36132* (2013.01); *A61N 1/37229*
        (2013.01)

(58) Field of Classification Search
    CPC .............. A61N 1/0424; A61N 1/36031; A61N
        1/36132; A61N 1/37229
    USPC ......................................................... 607/62
    See application file for complete search history.

(56)         References Cited

U.S. PATENT DOCUMENTS

| | | | |
|---|---|---|---|
| 5,099,838 | A | 3/1992 | Bardy |
| 5,113,869 | A | 5/1992 | Nappholz et al. |
| 5,324,328 | A | 6/1994 | Li et al. |
| 5,397,342 | A * | 3/1995 | Heil, Jr. ............... A61N 1/0587 |
| | | | 607/129 |
| 5,458,597 | A | 10/1995 | Edwards et al. |
| 5,582,609 | A * | 12/1996 | Swanson .............. A61B 5/6858 |
| | | | 606/39 |
| 5,630,426 | A | 5/1997 | Eggers et al. |
| 5,662,698 | A | 9/1997 | Altman et al. |
| 5,834,051 | A | 11/1998 | Woloszko et al. |
| 5,871,530 | A | 2/1999 | Williams et al. |
| 5,971,530 | A | 10/1999 | Hashimoto |
| 6,006,755 | A | 12/1999 | Edwards |
| 6,366,808 | B1 | 4/2002 | Schroeppel et al. |
| 6,569,159 | B1 | 5/2003 | Edwards et al. |
| 6,673,623 | B1 | 1/2004 | Huberman |
| 6,868,289 | B2 | 3/2005 | Palti |
| 6,920,361 | B2 | 7/2005 | Williams |
| 7,162,310 | B2 | 1/2007 | Doan |
| 7,449,021 | B2 | 11/2008 | Underwood et al. |
| 7,524,274 | B2 | 4/2009 | Patrick et al. |
| 7,565,205 | B2 | 7/2009 | Palti |
| 7,632,235 | B1 | 12/2009 | Karicherla et al. |
| 7,656,205 | B2 | 2/2010 | Chen et al. |
| 7,715,921 | B2 | 5/2010 | Palti |
| 7,720,549 | B2 | 5/2010 | Schroeppel et al. |
| 7,805,201 | B2 | 9/2010 | Palti |
| 7,809,441 | B2 * | 10/2010 | Kane .................. A61N 1/37288 |
| | | | 607/22 |
| 7,890,183 | B2 | 2/2011 | Palti et al. |
| 7,917,227 | B2 | 3/2011 | Palti |
| 8,002,821 | B2 | 8/2011 | Stinson |
| 8,019,414 | B2 | 9/2011 | Palti |
| 8,170,648 | B2 | 5/2012 | Field et al. |
| 8,175,698 | B2 | 5/2012 | Palti et al. |
| 8,229,555 | B2 | 7/2012 | Palti |
| RE43,618 | E | 8/2012 | Palti |
| 8,244,345 | B2 | 8/2012 | Palti |
| 8,262,575 | B2 | 9/2012 | Davies |
| 8,406,870 | B2 | 3/2013 | Palti |
| 8,447,395 | B2 | 5/2013 | Palti et al. |
| 8,447,396 | B2 | 5/2013 | Palti et al. |
| 8,465,533 | B2 | 6/2013 | Palti |
| 8,483,821 | B2 | 7/2013 | Averina et al. |
| 8,500,713 | B2 | 8/2013 | Ferek-Petric |
| 8,706,261 | B2 | 4/2014 | Palti |
| 8,715,203 | B2 | 5/2014 | Palti |
| 8,718,756 | B2 | 5/2014 | Palti |
| 8,764,675 | B2 | 7/2014 | Palti |
| 8,805,466 | B2 | 8/2014 | Salahieh et al. |
| 8,956,352 | B2 | 2/2015 | Mauch et al. |
| 9,005,100 | B2 | 4/2015 | Gnanashanmugam et al. |
| 9,023,090 | B2 | 5/2015 | Palti |

| | | | |
|---|---|---|---|
| 9,023,091 | B2 | 5/2015 | Palti |
| 9,039,674 | B2 | 5/2015 | Palti et al. |
| 9,056,203 | B2 | 6/2015 | Palti et al. |
| 9,179,974 | B2 | 11/2015 | Ku et al. |
| 9,248,278 | B2 | 2/2016 | Crosby et al. |
| 9,283,383 | B2 * | 3/2016 | Osypka .................. A61N 1/059 |
| 9,308,039 | B2 | 4/2016 | Azure |
| 9,387,323 | B2 | 7/2016 | Fleischhacker et al. |
| 9,427,278 | B2 | 8/2016 | Swanson |
| 9,440,068 | B2 | 9/2016 | Palti et al. |
| 9,474,486 | B2 | 10/2016 | Eliason et al. |
| 9,526,911 | B1 | 12/2016 | Azure et al. |
| 9,630,022 | B2 | 4/2017 | Bourke et al. |
| 9,655,669 | B2 | 5/2017 | Palti et al. |
| 9,750,934 | B2 | 9/2017 | Palti et al. |
| 9,833,617 | B2 | 12/2017 | Travers et al. |
| 9,877,781 | B2 | 1/2018 | Grasse et al. |
| 9,910,453 | B2 | 3/2018 | Wasserman et al. |
| 10,029,117 | B2 | 7/2018 | Bourke |
| 10,238,862 | B2 | 3/2019 | Cook et al. |
| 10,265,530 | B1 | 4/2019 | Perryman et al. |
| 10,376,177 | B2 | 8/2019 | Valvano et al. |
| 10,471,254 | B2 | 11/2019 | Sano et al. |
| 10,849,675 | B2 | 12/2020 | Wallace |
| 11,191,956 | B2 | 12/2021 | Giladi et al. |
| 11,331,493 | B2 | 5/2022 | Pivonka et al. |
| 11,338,135 | B2 | 5/2022 | Schmidt et al. |
| 11,420,049 | B2 | 8/2022 | Schmidt et al. |
| 11,607,542 | B2 | 3/2023 | Schmidt et al. |
| 11,691,006 | B2 | 7/2023 | Schmidt et al. |
| 11,712,561 | B2 | 8/2023 | Schmidt et al. |
| 11,850,422 | B2 | 12/2023 | Schmidt et al. |
| 11,883,655 | B2 | 1/2024 | Srivastava et al. |
| 12,109,412 | B2 | 10/2024 | Schmidt et al. |
| 12,186,553 | B2 | 1/2025 | Schmidt et al. |
| 12,403,306 | B2 | 9/2025 | Schmidt et al. |
| 2001/0044643 | A1 | 11/2001 | Litovitz |
| 2002/0026183 | A1 | 2/2002 | Simpson |
| 2002/0049485 | A1 | 4/2002 | Smits |
| 2002/0065544 | A1 | 5/2002 | Smits |
| 2003/0020416 | A1 | 1/2003 | Kobayashi |
| 2003/0069623 | A1 | 4/2003 | Stypulkowski |
| 2003/0204161 | A1 | 10/2003 | Ferek-Petric |
| 2004/0010290 | A1 * | 1/2004 | Schroeppel ............ A61N 1/205 |
| | | | 607/3 |
| 2004/0010303 | A1 | 1/2004 | Bolea et al. |
| 2004/0147969 | A1 | 7/2004 | Mann et al. |
| 2004/0162600 | A1 | 8/2004 | Williams |
| 2004/0176804 | A1 | 9/2004 | Palti |
| 2004/0215235 | A1 | 10/2004 | Jackson et al. |
| 2004/0215296 | A1 | 10/2004 | Ganz et al. |
| 2005/0004507 | A1 * | 1/2005 | Schroeppel ............ A61N 1/326 |
| | | | 604/20 |
| 2005/0043894 | A1 | 2/2005 | Fernandez |
| 2005/0096584 | A1 * | 5/2005 | Ferek-Petric .......... A61N 1/325 |
| | | | 604/20 |
| 2005/0222623 | A1 | 10/2005 | Kroll et al. |
| 2005/0222646 | A1 * | 10/2005 | Kroll ...................... A61N 1/326 |
| | | | 607/72 |
| 2005/0240173 | A1 | 10/2005 | Palti |
| 2005/0288730 | A1 | 12/2005 | Deem et al. |
| 2005/0288761 | A1 | 12/2005 | Brabec et al. |
| 2006/0024802 | A1 | 2/2006 | Muller et al. |
| 2006/0149341 | A1 | 7/2006 | Palti |
| 2006/0190053 | A1 * | 8/2006 | Dobak, III ......... A61N 1/36167 |
| | | | 607/40 |
| 2006/0259092 | A1 | 11/2006 | Spadgenske et al. |
| 2006/0259099 | A1 | 11/2006 | Goetz et al. |
| 2006/0282122 | A1 | 12/2006 | Palti |
| 2006/0282126 | A1 | 12/2006 | Fischbach et al. |
| 2007/0033660 | A1 | 2/2007 | Palti |
| 2007/0135861 | A1 | 6/2007 | Wallace et al. |
| 2007/0179550 | A1 | 8/2007 | Dennis et al. |
| 2007/0225766 | A1 | 9/2007 | Palti |
| 2007/0239213 | A1 | 10/2007 | Palti |
| 2007/0239244 | A1 * | 10/2007 | Morgan .................. A61N 1/059 |
| | | | 607/119 |
| 2007/0255340 | A1 | 11/2007 | Giftakis et al. |
| 2007/0270675 | A1 | 11/2007 | Kane et al. |

(56)                     References Cited

U.S. PATENT DOCUMENTS

| | | |
|---|---|---|
| 2007/0270916 A1 | 11/2007 | Fischell et al. |
| 2008/0058669 A1 | 3/2008 | Kroll |
| 2008/0058887 A1 | 3/2008 | Griffin et al. |
| 2008/0071265 A1 | 3/2008 | Azure |
| 2008/0071350 A1 | 3/2008 | Stinson et al. |
| 2008/0086073 A1 | 4/2008 | Mcdaniel |
| 2008/0097424 A1 | 4/2008 | Wizeman et al. |
| 2008/0154346 A1* | 6/2008 | Smith ...................... A61N 1/37 607/115 |
| 2008/0172116 A1 | 7/2008 | Mrva et al. |
| 2008/0195227 A1 | 8/2008 | Boling et al. |
| 2008/0208271 A1 | 8/2008 | Sih et al. |
| 2008/0275524 A1 | 11/2008 | Furness et al. |
| 2009/0076500 A1 | 3/2009 | Azure et al. |
| 2009/0192381 A1* | 7/2009 | Brockway .............. A61B 5/283 600/373 |
| 2009/0234211 A1* | 9/2009 | Li ......................... A61B 5/318 600/516 |
| 2010/0016936 A1* | 1/2010 | Stevenson .......... A61B 18/1492 607/116 |
| 2010/0168820 A1 | 7/2010 | Maniak et al. |
| 2010/0191311 A1 | 7/2010 | Scheiner et al. |
| 2010/0198298 A1 | 8/2010 | Schulman et al. |
| 2010/0217356 A1 | 8/2010 | Bikson et al. |
| 2010/0261994 A1* | 10/2010 | Davalos .............. A61B 18/1477 600/411 |
| 2010/0298895 A1 | 11/2010 | Ghaffari et al. |
| 2010/0331938 A1 | 12/2010 | Sommer et al. |
| 2011/0071608 A1 | 3/2011 | Fleischhacker et al. |
| 2011/0077717 A1* | 3/2011 | Poletto ................. A61N 1/3616 607/66 |
| 2011/0125215 A1 | 5/2011 | Goetz et al. |
| 2011/0137229 A1 | 6/2011 | Palti et al. |
| 2011/0224665 A1 | 9/2011 | Crosby et al. |
| 2011/0238057 A1 | 9/2011 | Moss et al. |
| 2011/0306878 A1* | 12/2011 | Desimone .............. A61N 1/325 600/431 |
| 2012/0035616 A1 | 2/2012 | Olsen et al. |
| 2012/0130444 A1 | 5/2012 | Wei et al. |
| 2012/0158072 A1 | 6/2012 | Venook et al. |
| 2012/0158122 A1 | 6/2012 | Mattson et al. |
| 2012/0203307 A1 | 8/2012 | Schroeppel et al. |
| 2012/0232615 A1 | 9/2012 | Barolat et al. |
| 2012/0283726 A1* | 11/2012 | Palti .......................... A61N 1/40 606/41 |
| 2013/0023946 A1 | 1/2013 | Valvano et al. |
| 2013/0165916 A1 | 6/2013 | Mathur et al. |
| 2013/0204068 A1 | 8/2013 | Gnanashanmugam et al. |
| 2013/0261706 A1* | 10/2013 | Mirro ................. A61N 1/36178 607/74 |
| 2013/0261711 A1 | 10/2013 | Sivo |
| 2013/0289649 A1 | 10/2013 | Averina et al. |
| 2013/0289664 A1 | 10/2013 | Johanek |
| 2013/0310898 A1 | 11/2013 | Ollivier et al. |
| 2014/0005753 A1* | 1/2014 | Carbunaru ......... A61N 1/37247 607/62 |
| 2014/0052227 A1 | 2/2014 | Wahlstrand et al. |
| 2014/0094888 A1 | 4/2014 | True et al. |
| 2014/0107511 A1 | 4/2014 | Banet et al. |
| 2014/0142670 A1 | 5/2014 | Radhakrishnan et al. |
| 2014/0276781 A1 | 9/2014 | Beani et al. |
| 2014/0276811 A1 | 9/2014 | Koblish et al. |
| 2014/0350541 A1 | 11/2014 | Hill et al. |
| 2014/0350653 A1 | 11/2014 | Shiroff et al. |
| 2015/0005804 A1 | 1/2015 | Franano et al. |
| 2015/0066024 A1 | 3/2015 | Azure |
| 2015/0119952 A1* | 4/2015 | Sharma ................. A61N 1/3606 607/40 |
| 2015/0134022 A1 | 5/2015 | Lee et al. |
| 2015/0180161 A1 | 6/2015 | Olson et al. |
| 2015/0182282 A1 | 7/2015 | Zemel et al. |
| 2015/0320995 A1 | 11/2015 | Nazareth et al. |
| 2015/0321000 A1 | 11/2015 | Rosenbluth et al. |
| 2015/0353916 A1* | 12/2015 | Subramaniam ........ C12N 13/00 435/39 |
| 2015/0374992 A1 | 12/2015 | Crosby et al. |
| 2016/0022986 A1* | 1/2016 | Travers .................... A61N 1/32 607/59 |
| 2016/0029960 A1 | 2/2016 | Toth et al. |
| 2016/0068598 A1 | 3/2016 | Yan et al. |
| 2016/0082258 A1 | 3/2016 | Kramer et al. |
| 2016/0121106 A1 | 5/2016 | Marshall et al. |
| 2016/0128767 A1 | 5/2016 | Azamian et al. |
| 2016/0129276 A1 | 5/2016 | Fried et al. |
| 2016/0175580 A1 | 6/2016 | Marshall et al. |
| 2016/0250476 A1 | 9/2016 | Kaemmerer et al. |
| 2016/0250483 A1 | 9/2016 | Klimovitch et al. |
| 2016/0278863 A1 | 9/2016 | Arai et al. |
| 2016/0331459 A1* | 11/2016 | Townley .................. A61N 7/00 |
| 2016/0346536 A1 | 12/2016 | Palti et al. |
| 2017/0007310 A1 | 1/2017 | Rajagopalan et al. |
| 2017/0035496 A1 | 2/2017 | Nagale et al. |
| 2017/0049514 A1 | 2/2017 | Cosman |
| 2017/0065339 A1 | 3/2017 | Mickelsen |
| 2017/0105793 A1 | 4/2017 | Cao et al. |
| 2017/0120041 A1 | 5/2017 | Wenger et al. |
| 2017/0173340 A1 | 6/2017 | Gupte et al. |
| 2017/0189098 A1 | 7/2017 | Azure et al. |
| 2017/0209691 A1 | 7/2017 | Sorajja |
| 2017/0215939 A1* | 8/2017 | Palti ...................... A61B 18/12 |
| 2017/0231694 A1 | 8/2017 | Mathur et al. |
| 2017/0251976 A1 | 9/2017 | Schouenborg |
| 2017/0266371 A1* | 9/2017 | Leonhardt .............. A61N 1/326 |
| 2017/0281934 A1* | 10/2017 | Giladi ...................... A61N 1/32 |
| 2017/0281955 A1* | 10/2017 | Maile .................. A61B 5/0422 |
| 2017/0312501 A1* | 11/2017 | Bornzin .............. A61N 1/0587 |
| 2017/0333702 A1 | 11/2017 | Barner |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0021563 A1 | 1/2018 | Van De Stolpe et al. |
| 2018/0050200 A1 | 2/2018 | Wasserman et al. |
| 2018/0104486 A1* | 4/2018 | Yoon .................. A61N 1/36002 |
| 2018/0110978 A1* | 4/2018 | Beebe .................. A61K 31/395 |
| 2018/0154142 A1 | 6/2018 | Guo et al. |
| 2018/0221088 A1 | 8/2018 | Govari et al. |
| 2018/0246079 A1 | 8/2018 | Wang et al. |
| 2018/0256906 A1 | 9/2018 | Pivonka et al. |
| 2018/0289954 A1 | 10/2018 | Hebb et al. |
| 2019/0008555 A1 | 1/2019 | O'Mahony |
| 2019/0117962 A1 | 4/2019 | Chiang et al. |
| 2019/0117970 A1 | 4/2019 | Schmidt et al. |
| 2019/0117971 A1 | 4/2019 | Schmidt et al. |
| 2019/0117972 A1 | 4/2019 | Schmidt et al. |
| 2019/0117973 A1 | 4/2019 | Schmidt et al. |
| 2019/0255344 A1* | 8/2019 | Carter ................ A61N 1/36002 |
| 2019/0262605 A1 | 8/2019 | Babakhani et al. |
| 2019/0321624 A1 | 10/2019 | De Kock et al. |
| 2019/0343398 A1 | 11/2019 | Zimmer |
| 2020/0009377 A1 | 1/2020 | Chang et al. |
| 2020/0061385 A1 | 2/2020 | Schwarz et al. |
| 2020/0197086 A1 | 6/2020 | Azamian et al. |
| 2020/0330756 A1 | 10/2020 | Schmidt et al. |
| 2020/0330757 A1 | 10/2020 | Schmidt et al. |
| 2020/0330758 A1 | 10/2020 | Schmidt et al. |
| 2020/0338344 A1 | 10/2020 | Schmidt et al. |
| 2020/0338345 A1 | 10/2020 | Schmidt et al. |
| 2020/0338346 A1 | 10/2020 | Schmidt et al. |
| 2021/0260370 A1 | 8/2021 | Srivastava et al. |
| 2021/0339015 A1 | 11/2021 | Dinsmoor et al. |
| 2022/0241586 A1 | 8/2022 | Spehr et al. |
| 2022/0288388 A1 | 9/2022 | Rondoni et al. |
| 2022/0296907 A1 | 9/2022 | Schmidt et al. |
| 2023/0218894 A1 | 7/2023 | Arnholt et al. |
| 2023/0330416 A1 | 10/2023 | Schmidt et al. |
| 2024/0024670 A1 | 1/2024 | Schmidt et al. |
| 2024/0115856 A1 | 4/2024 | Schmidt et al. |
| 2024/0226547 A1 | 7/2024 | Schmidt et al. |
| 2025/0099752 A1 | 3/2025 | Schmidt et al. |
| 2025/0345603 A1 | 11/2025 | Schmidt et al. |

(56) References Cited

U.S. PATENT DOCUMENTS

FOREIGN PATENT DOCUMENTS

| CN | 101693875 | 4/2010 |
| CN | 202365923 | 8/2012 |
| CN | 202844368 | 4/2013 |
| CN | 104955386 | 9/2015 |
| CN | 204698678 | 10/2015 |
| CN | 106823145 | 6/2017 |
| CN | 111278504 | 2/2025 |
| CN | 113766948 | 2/2025 |
| EP | 2942023 | 11/2015 |
| EP | 3700626 | 10/2024 |
| EP | 4445943 | 10/2024 |
| EP | 4480526 | 12/2024 |
| JP | 2011030734 | 2/2011 |
| TW | 201039699 | 11/2010 |
| WO | 9513113 | 5/1995 |
| WO | 9526911 | 10/1995 |
| WO | 9639966 | 12/1996 |
| WO | 0158371 | 8/2001 |
| WO | 0167098 | 9/2001 |
| WO | 2006047833 | 5/2006 |
| WO | 2008089360 | 7/2008 |
| WO | 2009036457 | 3/2009 |
| WO | 2009036459 | 3/2009 |
| WO | 2013052590 | 4/2013 |
| WO | 2014114433 | 7/2014 |
| WO | 2015100451 | 7/2015 |
| WO | 2015175570 | 11/2015 |
| WO | 2016065263 | 4/2016 |
| WO | 2016168485 | 10/2016 |
| WO | 2016179712 | 11/2016 |
| WO | 2016199142 | 12/2016 |
| WO | 2017123981 | 7/2017 |
| WO | 2018207103 | 11/2018 |
| WO | 2019084011 | 5/2019 |
| WO | 2023137008 | 7/2023 |

OTHER PUBLICATIONS

International Search Report and Written Opinion for PCT Application No. PCT/US2018/057104 mailed Dec. 20, 2018 (14 pages).
International Search Report and Written Opinion for PCT Application No. PCT/US2018/057115 mailed Jan. 4, 2019 (13 pages).
International Search Report and Written Opinion for PCT Application No. PCT/US2018/057120 mailed Dec. 19, 2018 (14 pages).
International Search Report and Written Opinion for PCT Application No. PCT/US2018/057127 mailed Jan. 18, 2019 (12 pages).
International Search Report and Written Opinion for PCT Application No. PCT/US2018/057117 mailed Dec. 20, 2018 (14 pages).
Di Sebastiano, Andrea R. et al., "Preclinical Outcomes of Intratumoral Modulation Therapy for Glioblastoma," Scientific Reports (2018) 8:7301 (11 pages).
Xu, Hu et al., "In Vitro Validation of Intratumoral Modulation Therapy for Glioblastoma," Anticancer Research 36:71-80 (2016), 10 pages.
International Preliminary Report on Patentability for PCT Application No. PCT/US2018/057104 mailed May 7, 2020 (8 pages).
International Preliminary Report on Patentability for PCT Application No. PCT/US2018/057115 mailed May 7, 2020 (9 pages).
International Preliminary Report on Patentability for PCT Application No. PCT/US2018/057117 mailed May 7, 2020 (8 pages).
International Preliminary Report on Patentability for PCT Application No. PCT/US2018/057120 mailed May 7, 2020 (8 pages).
International Preliminary Report on Patentability for PCT Application No. PCT/US2018/057127 mailed May 7, 2020 (8 pages).
Non-Final Office Action for U.S. Appl. No. 16/167,140 mailed Apr. 6, 2020 (28 pages).
Non-Final Office Action for U.S. Appl. No. 16/167,079 mailed Apr. 17, 2020 (36 pages).
Non-Final Office Action for U.S. Appl. No. 16/167,087 mailed May 27, 2020 (31 pages).
Response to Non-Final Rejection mailed on Apr. 17, 2020 for U.S. Appl. No. 16/167,079, submitted via EFS-Web on Jul. 7, 2020, 17 pages.
Response to Non-Final Rejection mailed on Apr. 6, 2020 for U.S. Appl. No. 16/167,140, submitted via EFS-Web on Jul. 6, 2020, 12 pages.
International Search Report and Written Opinion for PCT Application No. PCT/US2020/028508 mailed Aug. 3, 2020 (13 pages).
International Search Report and Written Opinion for PCT Application No. PCT/US2020/028509 mailed Jun. 30, 2020 (15 pages).
International Search Report and Written Opinion for PCT Application No. PCT/US2020/028512 mailed Jul. 13, 2020 (14 pages).
International Search Report and Written Opinion for PCT Application No. PCT/US2020/029270 mailed Oct. 26, 2020 (19 pages).
International Search Report and Written Opinion for PCT Application No. PCT/US2020/029274 mailed Aug. 28, 2020 (19 pages).
International Search Report and Written Opinion for PCT Application No. PCT/US2020/029277 mailed Jul. 13, 2020 (15 pages).
Invitation to Pay Additional Fees for PCT Application No. PCT/US2020/029270 mailed Aug. 28, 2020 (14 pages).
Invitation to Pay Additional Fees for PCT Application No. PCT/US2020/029274 mailed Jul. 7, 2020 (13 pages).
Kirson, Eilon D. et al., "Disruption of Cancer Cell Replication by Alternating Electric Fields," Cancer Research 64, 3288-3295, May 1, 2004 (8 pages).
Non-Final Office Action for U.S. Appl. No. 16/167,079 mailed Jan. 6, 2021 (28 pages).
Response to Communication Pursuant to Rules 161(1) and 162 EPC for European Patent Application No. 18800411.3 filed Dec. 9, 2020 (11 pages).
Response to Communication Pursuant to Rules 161(1) and 162 EPC for European Patent Application No. 18801134.0 filed Dec. 11, 2020 (9 pages).
Response to Communication Pursuant to Rules 161(1) and 162 EPC for European Patent Application No. 18801136.5 filed Dec. 10, 2020 (8 pages).
Response to Communication Pursuant to Rules 161(1) and 162 EPC for European Patent Application No. 18801137.3 filed Dec. 10, 2020 (7 pages).
Response to Communication Pursuant to Rules 161(1) and 162 EPC for European Patent Application No. 18801138.1 filed Dec. 11, 2020 (16 pages).
Response to Examination Report for Australian Patent Application No. 2018354149 filed Dec. 21, 2020 (14 pages).
Response to Examination Report for Australian Patent Application No. 2018354157 filed Dec. 31, 2020 (17 pages).
Response to Examination Report for Australian Patent Application No. 2018354159 filed Jan. 18, 2021 (21 pages).
Response to Final Rejection mailed on Oct. 13, 2020 for U.S. Appl. No. 16/167,087, 11 pages, submitted via EFS-Web on Jan. 13, 2021.
Response to Final Rejection mailed on Oct. 19, 2020 for U.S. Appl. No. 16/167,140, submitted via EFS-Web on Jan. 19, 2021, 16 pages.
Response to Non-Final Rejection mailed on Oct. 7, 2020 for U.S. Appl. No. 16/167,116, submitted via EFS-Web on Jan. 6, 2021, 13 pages.
Second Examination Report for Australian Patent Application No. 2018354149 mailed Jan. 8, 2021 (4 pages).
Final Office Action for U.S. Appl. No. 16/167,116 mailed Jan. 21, 2021 (25 pages).
Final Office Action for U.S. Appl. No. 16/167,079 mailed Sep. 15, 2020 (27 pages).
Final Office Action for U.S. Appl. No. 16/167,087 mailed Oct. 13, 2020 (21 pages).
Final Office Action for U.S. Appl. No. 16/167,140 mailed Oct. 19, 2020 (27 pages).
First Examination Report for Australian Patent Application No. 2018354149 mailed Jul. 29, 2020 (5 pages).
First Examination Report for Australian Patent Application No. 2018354157 mailed Jul. 31, 2020 (5 pages).
First Examination Report for Australian Patent Application No. 2018354159 mailed Aug. 12, 2020 (5 pages).

(56)        References Cited

OTHER PUBLICATIONS

First Examination Report for Australian Patent Application No. 2018354162 mailed Sep. 29, 2020 (8 pages).
First Examination Report for Australian Patent Application No. 2018354167 mailed Sep. 14, 2020 (5 pages).
Non-Final Office Action for U.S. Appl. No. 16/167,116 mailed Oct. 7, 2020 (40 pages).
Response to Final Rejection mailed on Sep. 15, 2020 for U.S. Appl. No. 16/167,079, submitted via EFS-Web on Nov. 5, 2020, 20 pages.
Response to Non-Final Rejection mailed on May 27, 2020 for U.S. Appl. No. 16/167,087, submitted via EFS-Web on Aug. 20, 2020, 10 pages.
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
"Optune®—Elevate Expectations / Patient Information and Operation Manual," Novocure™, www.optune.com, 46, pages, Jan. 2019.
Novocure Announces Launch of the inovitro™ Laboratory Research System, Press Release, 2 pages, Nov. 21, 2013.
Communication Pursuant to Article 94(3) EPC for European Patent Application No. 18801137.3 mailed Mar. 5, 2021 (4 pages).
Examination Report for Australian Patent Application No. 2018354162 mailed Feb. 4, 2021 (5 pages).
Office Action for Japanese Patent Application No. 2020-542718 mailed Feb. 9, 2021 11 pages) with English Translation.
Office Action for Japanese Patent Application No. 2020-542721 mailed Feb. 9, 2021 (5 pages) No. English Translation.
Office Action for Japanese Patent Application No. 2020-542722 mailed Feb. 9, 2021 (5 pages) with English Summary.
Response to Examination Report for Australian Patent Application No. 2018354162 filed Jan. 28, 2021 (15 pages).
Response to Examination Report for Australian Patent Application No. 2018354167 filed Jan. 28, 2021 (17 pages).
Response to Final Rejection mailed on Jan. 21, 2021 for U.S. Appl. No. 16/167,116, submitted via EFS-Web on Mar. 2, 2021, 12 pages.
"Communication Pursuant to Article 94(3) EPC," for European Patent Application No. 18801138.1 mailed Jun. 7, 2021 (7 pages).
"Examination Report," for Australian Patent Application No. 2018354162 mailed Apr. 21, 2021 (5 pages).
"Final Office Action," for U.S. Appl. No. 16/167,079 mailed Jun. 23, 2021 (34 pages).
"First Office Action," for Chinese Patent Application No. 201880068896.3 mailed Apr. 13, 2021 (17 pages) with English Summary.
"International Search Report and Written Opinion," for PCT Application No. PCT/US2021/019160 mailed Jun. 2, 2021 (15 pages).
"Non-Final Office Action," for U.S. Appl. No. 16/167,087 mailed Mar. 31, 2021 (28 pages).
"Non-Final Office Action," for U.S. Appl. No. 16/855,421 mailed May 28, 2021 (37 pages).
"Office Action," for Canadian Patent Application No. 3,079,289 mailed May 28, 2021 (4 pages).
"Response to Examination Report," for Australian Patent Application No. 2018354162 filed Mar. 30, 2021 (15 pages).
"Response to Non-Final Rejection," mailed on Jan. 6, 2021 for U.S. Appl. No. 16/267,079, submitted via EFS-Web on Apr. 6, 2021, 19 pages.
"Response to Non-Final Rejection," mailed on Mar. 31, 2021 for U.S. Appl. No. 16/167,087, submitted via EFS-Web on Jun. 23, 2021, 12 pages.
"Response to Second Examination Report," for Australian Patent Application No. 2018354149 filed Apr. 13, 2021 (19 pages).
"Office Action," for Japanese Patent Application No. 2020-542719 mailed Jun. 1, 2021 (9 pages) with English Translation.
"Office Action," for Japanese Patent Application No. 2020-542720 mailed May 11, 2021 (13 pages) with English Translation.
"Examination Report," for Canadian Patent Application No. 3,079,213 mailed Jul. 12, 2021 (4 pages).
"Examination Report," for Canadian Patent Application No. 3,079,282 mailed Jul. 14, 2021 (4 pages).

"Examination Report," for Canadian Patent Application No. 3,079,314 mailed Jul. 14, 2021 (4 pages).
"Final Office Action," for U.S. Appl. No. 16/167,087 mailed Aug. 2, 2021 (25 pages).
"Non-Final Office Action," for U.S. Appl. No. 16/167,116 mailed Sep. 3, 2021 (29 pages).
"Non-Final Office Action," for U.S. Appl. No. 16/167,140 mailed Jul. 12, 2021 (32 pages).
"Non-Final Office Action," for U.S. Appl. No. 16/850,720 mailed Aug. 24, 2021 (32 pages).
"Non-Final Office Action," for U.S. Appl. No. 16/855,433 mailed Sep. 8, 2021 (32 pages).
"Response to Examination Report," for Australian Patent Application No. 2018354162 filed Jul. 13, 2021 (18 pages).
"Response to Final Rejection," mailed on Jun. 23, 2021 for U.S. Appl. No. 16/167,079, submitted via EFS-Web on Sep. 9, 2021, 16 pages.
"Response to Non-Final Rejection," mailed on May 28, 2021 for U.S. Appl. No. 16/855,421, submitted via EFS-Web on Aug. 20, 2021, 11 pages.
"Communication Pursuant to Article 94(3) EPC," for European Patent Application No. 18801137.3 mailed Sep. 15, 2021 (4 pages).
"First Office Action," for Chinese Patent Application No. 201880078117.8 mailed Jul. 20, 2021 (14 pages) with English Summary.
"Response to Communication Pursuant to Article 94(3) EPC," for European Patent Application No. 18801138.1 filed Oct. 15, 2021 (10 pages).
"Response to Non-Final Rejection," mailed on Jul. 12, 2021 for U.S. Appl. No. 16/167,140, submitted via EFS-Web on Oct. 12, 2021, 16 pages.
"Response to Office Action," for Canadian Patent Application No. 3,079,289 filed with CIPO Sep. 23, 2021 (17 pages).
"Decision of Rejection," for Japanese Patent Application No. 2020-542719 mailed Oct. 19, 2021 (3 pages) No. English Translation.
"Final Office Action," for U.S. Appl. No. 16/855,421 mailed Nov. 5, 2021 (25 pages).
"International Preliminary Report on Patentability," for PCT Application No. PCT/US2020/028508 mailed Nov. 4, 2021 (8 pages).
"International Preliminary Report on Patentability," for PCT Application No. PCT/US2020/028509 mailed Nov. 4, 2021 (9 pages).
"International Preliminary Report on Patentability," for PCT Application No. PCT/US2020/028512 mailed Nov. 4, 2021 (8 pages).
"International Preliminary Report on Patentability," for PCT Application No. PCT/US2020/029270 mailed Nov. 4, 2021 (11 pages).
"International Preliminary Report on Patentability," for PCT Application No. PCT/US2020/029274 mailed Nov. 4, 2021 (13 pages).
"International Preliminary Report on Patentability," for PCT Application No. PCT/US2020/029277 mailed Nov. 4, 2021 (10 pages).
"Office Action," for Japanese Patent Application No. 2020-542718 mailed Oct. 19, 2021 (3 pages) No English Translation.
"Office Action," for Japanese Patent Application No. 2020-542722 mailed Oct. 26, 2021 (5 pages) No English Translation.
"Response to Final Rejection mailed on," Aug. 2, 2021 for U.S. Appl. No. 16/167,087, submitted via EFS-Web on Nov. 1, 2021, 12 pages.
"Response to Final Rejection," mailed on Jun. 23, 2021 and the Advisory Action mailed on Oct. 15, 2021 for U.S. Appl. No. 16/167,079, submitted via EFS-Web on Oct. 21, 2021, 19 pages.
"Response to Non-Final Rejection," mailed on Aug. 24, 2021 for U.S. Appl. No. 16/850,720, submitted via EFS-Web on Nov. 1, 2021, 11 pages.
"Response to Non-Final Rejection," mailed on Sep. 3, 2021 for U.S. Appl. No. 16/167,116, submitted via EFS-Web on Nov. 2, 2021, 14 pages.
"Response to Non-Final Rejection," mailed on Sep. 8, 2021 for U.S. Appl. No. 16/855,433, submitted via EFS-Web on Nov. 2, 2021, 12 pages.
"Second Office Action," for Chinese Patent Application No 201880068896.3 Oct. 20, 2021 (6 pages), No English translation.
"Decision of Rejection," for Japanese Patent Application No. 2020-54219 mailed Oct. 19, 2021 (6 pages) with English Translation.

(56) References Cited

OTHER PUBLICATIONS

"Final Office Action," for U.S. Appl. No. 16/167,140 mailed Dec. 27, 2021 (30 pages).
"Final Office Action," for U.S. Appl. No. 16/850,720 mailed Nov. 15, 2021 (15 pages).
"Final Office Action," for U.S. Appl. No. 16/855,433 mailed Feb. 1, 2022 (20 pages).
"Non-Final Office Action," for U.S. Appl. No. 16/167,079 mailed Feb. 17, 2022 (37 pages).
"Non-Final Office Action," for U.S. Appl. No. 16/167,087 mailed Dec. 22, 2021 (24 pages).
"Non-Final Office Action," for U.S. Appl. No. 16/850,712 mailed Jan. 21, 2022 (40 pages).
"Non-Final Office Action," for U.S. Appl. No. 17/182,436 mailed Feb. 1, 2022 (41 pages).
"Notice of Allowance," for U.S. Appl. No. 16/167,116 mailed Jan. 26, 2022 (19 pages).
"Office Action," for Japanese Patent Application No. 2020-542721 mailed Jan. 4, 2022 (3 pages) with English summary.
"Response to Communication Pursuant to Art. 94(3) EPC," for European Patent Application No. 18801137.3 filed Jan. 13, 2022 (8 pages).
"Response to Examination Report," for Canadian Patent Application No. 3,079,213 filed Nov. 10, 2021 (13 pages).
"Response to Examination Report," for Canadian Patent Application No. 3,079,282 filed Nov. 10, 2021 (13 pages).
"Response to Final Rejection," mailed on Dec. 27, 2021 for U.S. Appl. No. 16/167,140, submitted via EFS-Web on Feb. 9, 2022, 9 pages.
"Response to Final Rejection," mailed on Nov. 15, 2021 for U.S. Appl. No. 16/850,720, submitted via EFS-Web on Feb. 11, 2022, 12 pages.
"Response to Final Rejection," mailed on Nov. 5, 2021 and Advisory Action mailed on Feb. 9, 2022 for U.S. Appl. No. 16/855,421, submitted via EFS-Web on Mar. 4, 2022.
"Response to Final Rejection," mailed on Nov. 5, 2021 for U.S. Appl. No. 16/855,421, submitted via EFS-Web on Jan. 5, 2022, 11 pages.
"Response to Non-Final Rejection," mailed on Feb. 1, 2022 for U.S. Appl. No. 17/182,436, submitted via EFS-Web on Mar. 21, 2022, 8 pages.
"Response to Non-Final Rejection," mailed on Jan. 21, 2022 for U.S. Appl. No. 16/850,712, submitted via EFS-Web on Mar. 21, 2022, 10 pages.
"Response to Office Action," for Canadian Patent Application No. 3,079,314 filed Nov. 12, 2021 (14 pages).
"Response to Office Action," for Canadian Patent Application No. 3,079,316 filed Dec. 31, 2021 (15 pages).
"Communication Pursuant to Article 94(3) EPC," for European Patent Application No. 18801138.1 mailed Aug. 29, 2022 (5 pages).
"International Preliminary Report on Patentability," for PCT Application No. PCT/US2021/019160 mailed Sep. 9, 2022 (10 pages).
"Non-Final Office Action," for U.S. Appl. No. 16/167,087 mailed Sep. 15, 2022 (24 pages).
"Notice of Opposition," for European Patent No. 3700627 filed Aug. 24, 2022 (20 pages).
"Response to Final Rejection," mailed on Jul. 5, 2022 for U.S. Appl. No. 16/850,712, submitted via EFS-Web on Sep. 6, 2022, 10 pages.
"Response to Final Rejection," mailed on May 18, 2022 for U.S. Appl. No. 16/167,087, submitted via EFS-Web on Aug. 18, 2022, 9 pages.
"Response to Final Rejection," mailed on May 27, 2022 for U.S. Appl. No. 16/167,079, submitted via EFS-Web on Aug. 26, 2022, 12 pages.
"Response to Non-Final Rejection," mailed on Jun. 7, 2022 for U.S. Appl. No. 16/855,421, submitted via EFS-Web on Sep. 7, 2022, 9 pages.
"Response to Non-Final Rejection," mailed on May 27, 2022 for U.S. Appl. No. 16/167,140, submitted via EFS-Web on Aug. 25, 2022, 14 pages.

"Response to Non-Final Rejection," mailed on May 27, 2022 for U.S. Appl. No. 16/855,433, submitted via EFS-Web on Aug. 25, 2022, 9 pages.
"Third Office Action," for Japanese Patent Application No. 2020-542721 mailed Aug. 23, 2022 (9 pages) with English translation.
"Final Office Action," for U.S. Appl. No. 16/167,079 mailed May 27, 2022 (29 pages).
"Final Office Action," for U.S. Appl. No. 16/167,087 mailed May 18, 2022 (26 pages).
"Final Office Action," for U.S. Appl. No. 16/850,712 mailed Jul. 5, 2022 (16 pages).
"Final Office Action," for U.S. Appl. No. 17/182,436 mailed Jul. 27, 2022 (19 pages).
"International Search Report and Written Opinion," for PCT Application No. PCT/US2022/021161 mailed Jun. 22, 2022 (15 pages).
"Non-Final Office Action," for U.S. Appl. No. 16/167,140 May 27, 2022 (25 pages).
"Non-Final Office Action," for U.S. Appl. No. 16/855,421 mailed Jun. 7, 2022 (21 pages).
"Non-Final Office Action," for U.S. Appl. No. 16/855,433 mailed May 27, 2022 (18 pages).
"Notice of Allowance," for U.S. Appl. No. 16/850,720 mailed Apr. 14, 2022 (17 pages).
"Office Action Response," for Canadian Patent Application No. 3,079,289 filed Jul. 18, 2022 (17 pages).
"Office Action Response," for Canadian Patent Application No. 3,079,314 filed Aug. 11, 2022 (7 pages).
"Office Action," for Canadian Patent Application No. 3,079,213 mailed Apr. 20, 2022 (6 pages).
"Office Action," for Canadian Patent Application No. 3,079,289 mailed Mar. 24, 2022 (8 pages).
"Office Action," for Canadian Patent Application No. 3,079,314 mailed Apr. 29, 2022 (3 pages).
"Office Action," for Canadian Patent Application No. 3,079,316 mailed Jun. 3, 2022 (3 pages).
"Response to Communication Pursuant to Rules 161(1) and 162 EPC," for European Patent Application No. 20724332.0 filed May 11, 2022 (24 pages).
"Response to Communication Pursuant to Rules 161(1) and 162 EPC," for European Patent Application No. 20724702.4 filed May 11, 2022 (24 pages).
"Response to Communication Pursuant to Rules 161(1) and 162 EPC," for European Patent Application No. 20724703.2 filed Jun. 8, 2022 (12 pages).
"Response to Communication Pursuant to Rules 161(1) and 162 EPC," for European Patent Application No. 20727417.6 filed Jun. 1, 2022 (8 pages).
"Response to Communication Pursuant to Rules 161(1) and 162 EPC," for European Patent Application No. 20724333.8 filed Jun. 8, 2022 (8 pages).
"Response to Final Rejection," mailed on Dec. 27, 2021 and Advisory Action mailed on Mar. 9, 2022 for U.S. Appl. No. 16/167,140, submitted via EFS-Web on Mar. 25, 2022, 11 pages.
"Response to Final Rejection," mailed on Feb. 1, 2022 for U.S. Appl. No. 16/855,433, submitted via EFS-Web on May 2, 2022, 9 pages.
"Response to Non-Final Rejection," mailed on Dec. 22, 2021 for U.S. Appl. No. 16/167,087, submitted via EFS-Web on Mar. 22, 2022, 9 pages.
"Response to Non-Final Rejection," mailed on Feb. 17, 2022 for U.S. Appl. No. 16/167,079, submitted via EFS-Web on May 3, 2022, 11 pages.
"Response to Office Action," for Canadian Patent Application No. 3,079,213 filed Aug. 10, 2022 (10 pages).
Notice of Opposition for European Patent Application No. 18801134.0 on behalf of Novocure Gmbh, mailed Jun. 28, 2022 (36 pages).
"First Office Action," for Chinese Patent Application No. 201880068897.8 mailed Sep. 21, 2022 (11 pages) with English Summary.
"Non-Final Office Action," for U.S. Appl. No. 16/850,712 mailed Oct. 6, 2022 (11 pages).

(56) References Cited

OTHER PUBLICATIONS

"Response to Final Rejection," mailed on Jul. 22, 2022 with Request for Continued Examination, for U.S. Appl. No. 17/182,436, submitted via EFS-Web on Sep. 29, 2022, 9 pages.

"Response to Final Rejection," mailed on Jul. 27, 2022 for U.S. Appl. No. 17/182,436, submitted via EFS-Web on Sep. 27, 2022, 9 pages.

"Response to Final Rejection," mailed on Jul. 5, 2022 and Advisory Action mailed on Sep. 15, 2022 for U.S. Appl. No. 16/850,712, submitted via EFS-Web on Sep. 23, 2022, 10 pages.

"Communication Pursuant to Article 94(3) EPC," for European Patent Application No. 18800411.3 mailed Dec. 22, 2022 (5 pages).

"Non-Final Office Action," for U.S. Appl. No. 16/850,728 mailed Jan. 24, 2023 (68 pages).

"Notice of Allowance," for U.S. Appl. No. 16/850,712 Mailed Feb. 7, 2023 (14 pages).

"Office Action," for Canadian Patent Application No. 3,079,213 mailed Dec. 5, 2022 (4 pages).

"Office Action," for Japanese Patent Application No. 2021-562795 mailed Nov. 15, 2022 (5 pages) with English Translation.

"Office Action," for Japanese Patent Application No. 2021-562797 mailed Nov. 22, 2022 (9 pages), with English Translation.

"Office Action," for Japanese Patent Application No. 2021-562798 mailed Nov. 15, 2022 (14 pages), with English translation.

"Office Action," for Japanese Patent Application No. 2021-562966 mailed Nov. 29, 2022 (8 pages) with English summary.

"Office Action," for Japanese Patent Application No. 2021-562972 mailed Nov. 8, 2022 (26 pages) with English Translation.

"Response to Communication Pursuant to Rules 161(1) and 162 EPC," for European Patent Application No. 21712639.0 filed Jan. 20, 2023 (26 pages).

"Response to Non-Final Rejection," mailed on Nov. 7, 2022 for U.S. Appl. No. 16/855,448, submitted via EFS-Web on Feb. 7, 2023, 9 pages.

"Response to Non-Final Rejection," mailed on Oct. 6, 2022 for U.S. Appl. No. 16/850,712, submitted via EFS-Web on Jan. 4, 2023,10 pages.

"Response to Non-Final Rejection," mailed on Sep. 15, 2022 for U.S. Appl. No. 16/167,087, submitted via EFS-Web on Dec. 13, 2022, 8 pages.

"Non-Final Office Action," for U.S. Appl. No. 16/167,140 Nov. 15, 2022 (29 pages).

"Non-Final Office Action," for U.S. Appl. No. 16/855,433 mailed Nov. 17, 2022 (39 pages).

"Non-Final Office Action," for U.S. Appl. No. 16/855,448 mailed Nov. 7, 2022 (58 pages).

"Non-Final Office Action," for U.S. Appl. No. 17/182,436 mailed Nov. 23, 2022 (19 pages).

"Notice of Allowance," for U.S. Appl. No. 16/855,421 mailed Nov. 16, 2022 (17 pages).

"Office Action," for Canadian Patent Application No. 3,079,289 mailed Nov. 28, 2022 (7 pages).

"Communication Pursuant to Article 94(3) EPC," for European Patent Application No. 18801138.1 mailed Jul. 7, 2023 (5 pages).

"Office Action," for Canadian Patent Application No. 3,079,289 mailed Jul. 6, 2023 (3 pages).

"Office Action," for Japanese Patent Application No. 2021-562972 mailed May 5, 2023 (12 pages), with English translation.

"Response to Communication Pursuant to Article 94(3) EPC," for European Patent Application No. 20724333.8 filed Jul. 25, 2023 (28 pages).

"Response to Final Rejection," mailed on May 3, 2023, for U.S. Appl. No. 16/855,433, submitted via EFS-Web on Aug. 2, 2023, 10 pages.

"Second Office Action," for Japanese Patent Application No. 2021-562966 mailed Jun. 13, 2023 (9 pages), with English translation.

"Third Office Action," for Chinese Patent Application No. 201880068897.8 mailed Jun. 9, 2023 (10 pages) with English Summary.

"Communication Pursuant to Article 94(3) EPC," for European Patent Application No. 20724333.8 mailed Mar. 17, 2023 (6 pages).

"Decision of Rejection," for Japanese Patent Application No. 2021-562795 mailed Mar. 28, 2023 (6 pages) with English translation.

"Decision of Rejection," for Japanese Patent Application No. 2021-562797 mailed May 16, 2023 (10 pages), with English translation.

"Final Office Action," for Japanese Patent Application No. 2020-542721 mailed Mar. 7, 2023 (5 pages) with English translation.

"Final Office Action," for U.S. Appl. No. 16/167,087 mailed Mar. 6, 2023 (30 pages).

"Final Office Action," for U.S. Appl. No. 16/167,140 mailed May 24, 2023 (41 pages).

"Final Office Action," for U.S. Appl. No. 16/850,728 mailed Jun. 26, 2023 (26 pages).

"Final Office Action," for U.S. Appl. No. 16/855,433 mailed May 3, 2023 (25 pages).

"Final Office Action," for U.S. Appl. No. 17/182,436 mailed May 19, 2023 (22 pages).

"First Office Action," for Chinese Patent Application No. 201880068852.0 mailed Mar. 15, 2023 (9 pages).

"First Office Action," for Chinese Patent Application No. 201880078118.2 mailed Mar. 27, 2023 (17 pages) with English translation.

"International Search Report and Written Opinion," for PCT Application No. PCT/US2023/010469 mailed Apr. 12, 2023 (19 pages).

"Non-Final Office Action," for U.S. Appl. No. 16/167,079 mailed Mar. 23, 2023 (40 pages).

"Notice of Allowance," for U.S. Appl. No. 16/855,448 mailed Mar. 8, 2023 (19 pages).

"Response to Communication Pursuant to Article 94(3) EPC," for European Patent Application No. 18800411.3 filed May 2, 2023 (11 pages).

"Response to Communication Pursuant to Article 94(3) EPC," for European Patent Application No. 18801138.1 filed Mar. 8, 2023 (10 pages).

"Response to Final Rejection," mailed Mar. 6, 2023 for U.S. Appl. No. 16/167,087, submitted via EFS-Web on Jun. 6, 2023, 10 pages.

"Response to Non-Final Rejection," for U.S. Appl. No. 16/855,433, mailed on Nov. 17, 2022, submitted via EFS-Web on Feb. 17, 2023, 11 pages.

"Response to Non-Final Rejection," mailed on Jan. 24, 2023 for U.S. Appl. No. 16/850,728, submitted via EFS-Web on Apr. 20, 2023, 8 pages.

"Response to Non-Final Rejection," mailed on Mar. 23, 2023 for U.S. Appl. No. 16/167,079, submitted via EFS-Web on Jun. 23, 2023, 12 pages.

"Response to Non-Final Rejection," mailed on Nov. 15, 2022, based on U.S. Appl. No. 16/167,140, submitted via EFS-Web on Feb. 15, 2023, 12 pages.

"Response to Non-Final Rejection," mailed on Nov. 23, 2022 for U.S. Appl. No. 17/182,436, submitted via EFS-Web on Feb. 23, 2023, 11 pages.

"Response to Office Action," for Canadian Patent Application No. 3,079,213 filed Mar. 8, 2023 (6 pages).

"Response to Office Action," for Canadian Patent Application No. 3,079,289 filed Mar. 24, 2023 (18 pages).

"Second Office Action," for Chinese Patent Application No. 201880068897.8 mailed Feb. 27, 2023 (9 pages) with English Summary.

"Second Office Action," for Japanese Patent Application No. 2021-562798 mailed May 9, 2023 (11 pages) with English translation.

"Decision of Rejection," for Japanese Patent Application No. 2021-562972 mailed Sep. 5, 2023 (10 pages) with English Translation.

"Final Office Action," for U.S. Appl. No. 16/167,079 mailed Sep. 14, 2023 (33 pages).

"Fourth Office Action," for Chinese Patent Application No. 201880068897.8 mailed Oct. 17, 2023 (13 pages) with English Summary.

"International Preliminary Report on Patentability," for PCT Application No. PCT/US2022/021161 mailed Oct. 5, 2023 (9 pages).

"Non-Final Office Action," for U.S. Appl. No. 16/167,087 mailed Sep. 19, 2023 (38 pages).

(56) References Cited

OTHER PUBLICATIONS

"Non-Final Office Action," for U.S. Appl. No. 16/167,140 mailed Oct. 11, 2023 (32 pages).

"Notice of Allowance," for U.S. Appl. No. 16/855,433 mailed Aug. 23, 2023 (6 pages).

"Notice of Allowance," for U.S. Appl. No. 17/182,436 mailed Sep. 15, 2023 (17 pages).

"Office Action," for Japanese Patent Application No. 2021-562798 mailed Aug. 22, 2023 (4 pages) with English translation.

"Response to Final Office Action," mailed May 24, 2023, and Advisory Action mailed Sep. 20, 2023, for U.S. Appl. No. 16/167,140, submitted via EFS-Web on Sep. 25, 2023, 12 pages.

"Response to Final Rejection," mailed on Jun. 26, 2023 for U.S. Appl. No. 16/850,728, submitted via EFS-Web on Sep. 26, 2023, 11 pages.

"Response to Final Rejection," mailed on May 19, 2023, for U.S. Appl. No. 17/182,436, submitted via EFS-Web on Aug. 21, 2023, 14 pages.

"Response to Final Rejection," mailed on May 24, 2023, for U.S. Appl. No. 16/167,140, submitted via EFS-Web on Aug. 24, 2023, 11 pages.

"Response to Office Action," for Canadian Patent Application No. 3,079,289 filed Nov. 3, 2023 (13 pages).

"Summons to Attend Oral Proceedings," for European Patent Application No. 18801136.5 mailed Sep. 12, 2023 (13 pages).

"Supplemental Response to," Final Rejection mailed on Mar. 6, 2023, for U.S. Appl. No. 16/167,087, submitted via EFS-Web on Aug. 31, 2023, 7 pages.

"Zenchi Examination Report," for Japanese Patent Application No. 2021-562795 mailed Aug. 2, 2023 (9 pages) with English Summary.

"Final Office Action," for U.S. Appl. No. 16/167,140 mailed Feb. 7, 2024 (42 pages).

"First Office Action," for Chinese Patent Application No. 202080030771.9 mailed Nov. 15, 2023 (7 pages) with English summary.

"Response to Communication Pursuant to Article 94(3) EPC," for European Patent Application No. 18801138.1 filed Nov. 16, 2023 (76 pages).

"Response to Final Rejection," mailed on Sep. 14, 2023, for U.S. Appl. No. 16/167,079, submitted via EFS-Web on Dec. 14, 2023, 14 pages.

"Response to Non-Final Rejection," mailed on Oct. 11, 2024, for U.S. Appl. No. 16/167,140, submitted via EFS-Web on Jan. 11, 2024, 12 pages.

"Response to Non-Final Rejection," mailed on Sep. 19, 2023, for U.S. Appl. No. 16/167,087, submitted via EFS-Web on Dec. 19, 2023, 13 pages.

"Second Office Action," for Chinese Patent Application No. 201880078118.2 mailed Jan. 12, 2024 (17 pages) with English translation.

"Written Submissions," as filed in response to Summons to Attend Oral Proceedings for European Patent Application No. 18801134.0 filed Dec. 20, 2023 (137 pages).

"Decision of Rejection," for Japanese Patent Application No. 2021-562966 mailed Dec. 26, 2023 (9 pages), with English translation.

"Fifth Office Action," for Chinese Patent Application No. 201880068897.8 mailed Feb. 8, 2024 (8 pages) with English summary.

"First Office Action," for Chinese Patent Application No. 202080030769.1 mailed Dec. 29, 2023, with English summary (12 pages).

"Non-Final Office Action," for U.S. Appl. No. 16/850,728 mailed Feb. 14, 2024 (33 pages).

"Non-Final Office Action," for U.S. Appl. No. 17/698,516 mailed Feb. 23, 2024 (69 pages).

"Non-Final Office Action," for U.S. Appl. No. 18/123,776 mailed Mar. 20, 2024 (40 pages).

"Second Office Action," for Chinese Patent Application No. 201880068852.0 mailed Jan. 15, 2024 (19 pages) with English summary.

Chen, Yu, et al. "Synergistic chemo-photodynamic therapy mediated by light-activated ROS-degradable nanocarriers.," Synergistic chemo-photodynamic therapy mediated by light-activated ROS-degradable nanocarriers. J. Mater. Chem. B, 2019, 7, 460-468. Apr. 12, 2018 (Chen et al) https://pubs.rsc.org/en/content/articlelanding/20 I 9/tb/c8tb03030h, 460-468.

"Communication Pursuant to Article 94(3) EPC," for European Patent Application No. 20724703.2 mailed Jun. 4, 2024 (7 pages).

"Extended European Search Report," for European Patent Application No. 24159633.7 mailed Jun. 14, 2024 (7 pages).

"Extended European Search Report," for European Patent Application No. 24171875.8 mailed Jul. 16, 2024 (8 pages).

"Final Office Action," for U.S. Appl. No. 17/698,516 mailed Aug. 19, 2024 (25 pages).

"Final Rejection Action," for Chinese Patent Application No. 201880068852.0 mailed Jun. 7, 2024 (16 pages) with English Summary.

"International Preliminary Report on Patentability," for PCT Patent Application No. PCT/US2023/010469 mailed Jul. 25, 2024 (12 pages).

"Non-Final Office Action," for U.S. Appl. No. 18/215,603 mailed Jul. 18, 2024, 64 pages.

"Non-Final Office Action," for U.S. Appl. No. 18/227,021 mailed May 31, 2024 (61 pages).

"Notice of Allowance," for U.S. Appl. No. 16/850,728 mailed Jun. 5, 2024 (17 pages).

"Office Action," for Japanese Patent Application No. 2021-562795 mailed Jun. 18, 2024 (8 pages) with English translation.

"Response to Final Rejection," mailed Feb. 7, 2024, and the Advisory Action mailed on Jun. 4, 2024, for U.S. Appl. No. 16/167,140, submitted via EFS-Web on Jul. 2, 2024, 14 pages.

"Response to Non-Final Rejection," mailed on Apr. 25, 2024, for U.S. Appl. No. 16/167,079, submitted via EFS-Web on Jul. 25, 2024, 16 pages.

"Response to Non-Final Rejection," mailed on Mar. 20, 2024, for U.S. Appl. No. 18/123,776, submitted via EFS-Web on Jun. 20, 2024, 8 pages.

"Second Office Action," for Chinese Patent Application No. 202080030769.1 mailed Jul. 4, 2024 (13 pages) with English translation.

"Zenchi Examination Report," for Japanese Patent Application No. 2021-562966 mailed Aug. 6, 2024 (3 pages) with English Translation.

"Extended European Search Report," for European Patent Application No. 24171838.6 mailed May 8, 2024 (6 pages).

"Final Office Action," for U.S. Appl. No. 16/167,087 mailed Apr. 1, 2024 (38 pages).

"Final Rejection Action," for Chinese Patent Application No. 201880078118.2 mailed Mar. 28, 2024 (10 pages) with English translation, 12 pages.

"First Office Action," for Chinese Patent Application No. 202080030415.7 mailed Mar. 6, 2024 (13 pages) with English translation.

"First Office Action," for Chinese Patent Application No. 202080030850.X mailed Mar. 29, 2024 (14 pages) with English translation.

"First Office Action," for Chinese Patent Application No. 202080030856.7 mailed Mar. 16, 2024 (11 pages) with English translation.

"Non-Final Office Action," for U.S. Appl. No. 16/167,079 mailed Apr. 25, 2024 (34 pages).

"Response to Final Rejection," mailed on Feb. 7, 2024, for U.S. Appl. No. 16/167,140, submitted via EFS-Web on May 7, 2024, 12 pages.

"Response to Non-Final Rejection," mailed on Feb. 14, 2024, for U.S. Appl. No. 16/850,728, submitted via EFS-Web on May 14, 2024, 12 pages.

"Response to Non-Final Rejection," mailed on Feb. 23, 2024, for U.S. Appl. No. 17/698,516, submitted via EFS-Web on May 20, 2024, 9 pages.

"Final Office Action," for U.S. Appl. No. 16/167,079 mailed Sep. 6, 2024 (40 pages).

(56) References Cited

OTHER PUBLICATIONS

"Final Office Action," for U.S. Appl. No. 18/227,021 mailed Sep. 18, 2024 (15 pages).

"Notice of Allowance," for U.S. Appl. No. 18/123,776 mailed Sep. 9, 2024 (13 pages).

"Response to Communication Pursuant to Article 94(3) EPC," for European Patent Application No. 20724703.2 filed Sep. 25, 2024 (27 pages).

"Response to Final Rejection," mailed on Jun. 18, 2024, for U.S. Appl. No. 16/167,087, submitted via Patent Center on Sep. 17, 2024, 12. pages.

"Response to Non-Final Rejection," mailed on May 31, 2024, for U.S. Appl. No. 18/227,021, submitted via EFS-Web on Sep. 3, 2024, 8 pages.

"Supplemental Amendment," filed in response to Non-Final Rejection mailed Mar. 20, 2024, for U.S. Appl. No. 18/123,776, submitted via Patent center on Aug. 30, 2024, 12 pages.

Santhosh, Sheeba, et al."Impact of Electrodes Separation Distance on Bio-impedance Diagnosis.," Biomedical & Pharmacology Journal, Mar. 2021. 14(1), p. 141-146. (Year: 2021).

"Extended European Search Report," for European Patent Application No. 24191767.3 mailed Nov. 13, 2024 (10 pages).

"Extended European Search Report," for European Patent Application No. 24205287.6 mailed Feb. 7, 2025 (9 pages).

"Final Rejection," for Chinese Patent Application No. 202080030856.7 mailed Jan. 21, 2025 (7 pages) with English summary.

"Non-Final Office Action," for U.S. Appl. No. 16/167,079 mailed Dec. 27, 2024 (124 pages).

"Non-Final Office Action," for U.S. Appl. No. 16/167,087 mailed Feb. 18, 2025 (50 pages).

"Non-Final Office Action," for U.S. Appl. No. 16/167,140 mailed Mar. 10, 2025 (42 pages).

"Non-Final Office Action," for U.S. Appl. No. 18/227,021 mailed Mar. 6, 2025 (15 pages).

"Non-Final Rejection," mailed on Nov. 7, 2024, for U.S. Appl. No. 16/167,140, 50 pages.

"Notice of Allowance," for U.S. Appl. No. 18/215,603 mailed Jan. 23, 2025 (11 pages).

"Response to Extended European Search Report," for European Patent Application No. 24171875.8 filed Feb. 17, 2025 (24 pages).

"Response to Final Rejection mailed on," Sep. 18, 2024, for U.S. Appl. No. 18/227,021 submitted via Patent Center on Dec. 18, 2024, 10 pages.

"Response to Final Rejection," mailed Aug. 19, 2024, for U.S. Appl. No. 17/968,516, submitted via Patent Center on Dec. 4, 2024, 12 pages.

"Response to Final Rejection," mailed on Aug. 19, 2024, for U.S. Appl. No. 17/698,516, submitted via Patent Center on Nov. 12, 2024, 12 pages.

"Response to Final Rejection," mailed on Sep. 6, 2024, for U.S. Appl. No. 16/167,079, submitted via Patent Center on Dec. 6, 2024, 14 pages.

"Response to Non-Final Rejection," mailed on Jul. 18, 2024, for U.S. Appl. No. 18/215,603, submitted via Patent Center on Oct. 17, 2024, 8 pages.

"Response to Non-Final Rejection," mailed on Nov. 7, 2024, for U.S. Appl. No. 16/167,140, submitted via EFS-Web on Feb. 7, 2025, 11 pages.

"Second Office Action," for Chinese Patent Application No. 202080030850.X mailed Nov. 12, 2024, 8 pages.

"Second Office Action," for Chinese Patent Application No. 202080030856.7 mailed Nov. 9, 2024, 9 pages.

Schneiderman, et al., "Overcoming cell size escape from tumor treating fields using a varying frequency treatment paradigm in vitro," Meeting Abstract: 2013 ASCO Annual Meeting I; Journal of Clinical Oncology, 2013, 31(15): 2 pages.

"Corrected Notice of Allowability," for U.S. Appl. No. 18/215,603 mailed Apr. 30, 2025 (5 pages).

"Non-Final Office Action," for U.S. Appl. No. 18/543,879 mailed Jul. 28, 2025 (63 pages).

"Notice of Allowance," for U.S. Appl. No. 16/167,079 mailed May 28, 2025, 16 pages.

"Office Action," for Japanese Patent Application No. 2021-562966 mailed Jul. 22, 2025 (10 pages) with English summary.

"Response to Extended European Search Report," for European Patent Application No. 24191767.3 filed Jun. 10, 2025 (19 pages).

"Response to Non-Final Rejection," mailed on Dec. 27, 2024 for U.S. Appl. No. 16/167,079, submitted via Patent Center on Mar. 27, 2025, 15 pages.

"Response to Non-Final Rejection," mailed on Mar. 10, 2025, for U.S. Appl. No. 16/167,140, submitted via Patent Center on Jun. 10, 2025, 11 pages.

"First Office Action," for Chinese Patent Application No. 202180013870.0 mailed Aug. 2, 2025 (8 pages) with English Summary.

"Response to Non-Final Rejection," mailed on Jul. 28, 2025, for U.S. Appl. No. 18/543,879, submitted via Patent Center on Oct. 28, 2025, 10 pages.

"Final Office Action," for U.S. Appl. No. 18/543,879 mailed Jan. 26, 2026 (19 pages).

\* cited by examiner

100

106

326

104

328

330

306

336

308  310  312

320

314  316  318

324

322

302

102

332        304        334

400

406

402

404

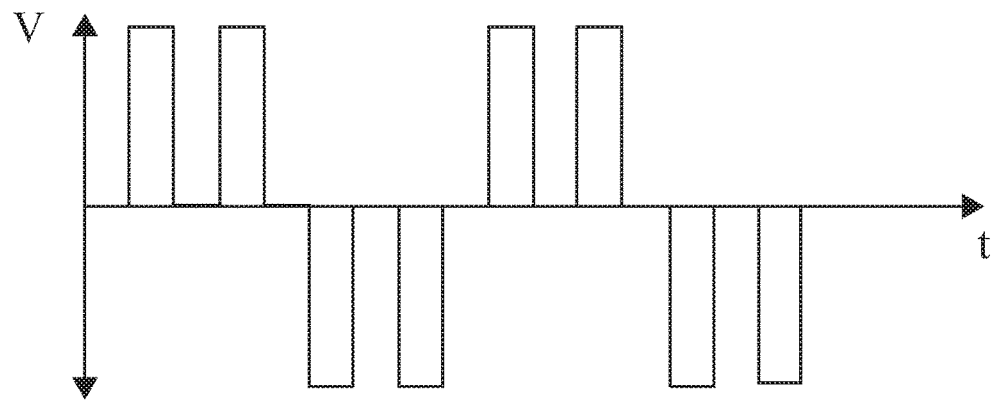
FIG. 26
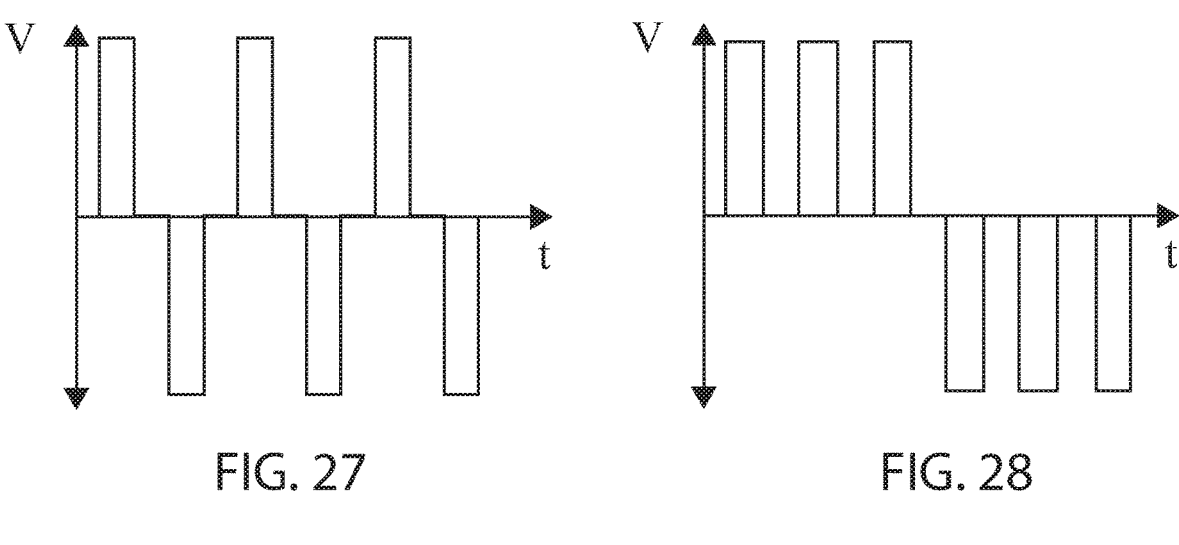
FIG. 27                    FIG. 28
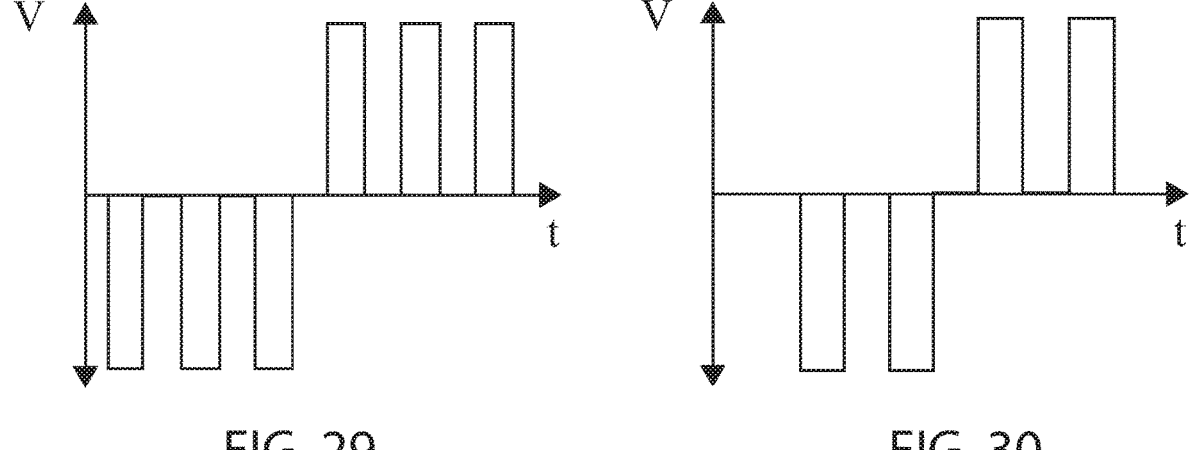
FIG. 29                    FIG. 30

MEDICAL DEVICES FOR TREATMENT OF CANCER WITH ELECTRIC FIELDS

This application claims the benefit of U.S. Provisional Application No. 62/575,681, filed Oct. 23, 2017, the content of which is herein incorporated by reference in its entirety.

FIELD

Embodiments herein relate to medical devices and methods for using the same to treat cancerous tumors within a bodily tissue. More specifically, embodiments herein relate to using medical devices configured to generate therapeutic electric fields at the site of a cancerous tumor.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

Mitosis is the process of cellular division that is a part of the cell cycle for all somatic cells in the body, including many types of cancerous cells. Mitosis includes four basic phases: prophase, metaphase, anaphase, and telophase. Just prior to prophase, a cell will copy its chromosomes to create two identical sister chromatids. During prophase, the chromosomes start to condense and the nuclear membrane surrounding the nucleus disappears. The mitotic spindle also begins to form during prophase. The mitotic spindle includes a self-organized bipolar array of microtubules and centrosomes. Microtubules are generally formed from the polymerization of the highly polar alpha-tubulin and beta-tubulin proteins. Centrosomes are similarly protein-based organelles, two of which migrate to opposite sides of the dividing cell at this phase. The negatively charged end of the microtubules attach to the centrosomes. The positively charged end of the microtubules radiate toward the equator of the dividing cell where they eventually attach to a kinetochore of each sister chromatid. Metaphase can be defined by all chromosomes being aligned at the equator of the dividing cell and bound in the mitotic spindle. An equal number of sister chromatids are then pulled toward opposite ends of the cell during anaphase. Once all chromosomes have been separated, the process of telophase begins, where the cell membrane begins to form a cleavage furrow between the two newly forming sister cells, and cell division becomes complete once the cells physically separate from one another in a process called cytokinesis.

SUMMARY

Embodiments herein relate to medical devices and methods for using the same to treat cancerous tumors within a bodily tissue. In a first aspect, in addition to one or more of the preceding or following aspects, or in the alternative to some aspects, a medical device is included. The medical device can include an electric field generating circuit configured to generate one or more electric fields and control circuitry in communication with the electric field generating circuit. The control circuitry can be configured to control delivery of the one or more electric fields from the electric field generating circuit. The control circuitry can cause the electric field generating circuit to generate one or more electric fields at frequencies selected from a range of between 10 kHz to 1 MHz at the site of a cancerous tumor located within a bodily tissue.

In a second aspect, in addition to one or more of the preceding or following aspects, or in the alternative to some aspects, the medical device can be configured to be implanted entirely within the body.

In a third aspect, in addition to one or more of the preceding or following aspects, or in the alternative to some aspects, the medical device can be configured to be partially implanted within the body.

In a fourth aspect, in addition to one or more of the preceding or following aspects, or in the alternative to some aspects, the one or more electric fields are can be effective to prevent and/or disrupt cellular mitosis in a cancerous cell.

In a fifth aspect, in addition to one or more of the preceding or following aspects, or in the alternative to some aspects, the one or more electric fields can be delivered along more than one vector, the vectors spatially separated by at least 10 degrees. In a sixth aspect, in addition to one or more of the preceding or following aspects, or in the alternative to some aspects, the electric field generating circuit can generate one or more electric fields at one or more frequencies selected from a range of between 100 kHz to 500 kHz.

In a seventh aspect, in addition to one or more of the preceding or following aspects, or in the alternative to some aspects, the electric field generating circuit can generate one or more electric fields at one or more frequencies selected from a range of between 100 kHz to 300 kHz.

In an eighth aspect, in addition to one or more of the preceding or following aspects, or in the alternative to some aspects, where the one or more leads are in electrical communication with the electric field generating circuit.

In a ninth aspect, in addition to one or more of the preceding or following aspects, or in the alternative to some aspects, the one or more leads each can include one or more electrodes in electrical communication with the electric field generating circuit.

In a tenth aspect, in addition to one or more of the preceding or following aspects, or in the alternative to some aspects, the one or more electric fields can be delivered along at least one vector including at least one of the electrodes.

In an eleventh aspect, in addition to one or more of the preceding or following aspects, or in the alternative to some aspects, the medical device including a housing in which the electric field generating circuit and the control circuitry are disposed, where the housing can include a portion that is in electrical communication with the electric field generating circuit to serve as an electrode.

In a twelfth aspect, in addition to one or more of the preceding or following aspects, or in the alternative to some aspects, the one or more electric fields can be delivered along at least one vector including a portion of the housing serving as an electrode.

In a thirteenth aspect, in addition to one or more of the preceding or following aspects, or in the alternative to some aspects, the control circuitry can be further configured to generate one or more electric fields by sweeping through one or more frequencies.

In a fourteenth aspect, in addition to one or more of the preceding or following aspects, or in the alternative to some aspects, where sweeping through one or more frequencies can include sweeping from a first frequency up to a second frequency and sweeping from the second frequency down to the first frequency, wherein the second frequency is higher than the first frequency.

In a fifteenth aspect, in addition to one or more of the preceding or following aspects, or in the alternative to some aspects, where sweeping from a first frequency up to a second frequency and sweeping from the second frequency down to the first frequency is repeated throughout the duration of the generating the one or more electric fields with the electric field generating circuit.

In a sixteenth aspect, in addition to one or more of the preceding or following aspects, or in the alternative to some aspects, where the control circuitry can be further configured to generate one or more electric fields by stacking one or more frequencies simultaneously.

In a seventeenth aspect, in addition to one or more of the preceding or following aspects, or in the alternative to some aspects, the one or more frequencies have an identical amplitude.

In an eighteenth aspect, in addition to one or more of the preceding or following aspects, or in the alternative to some aspects, the one or more frequencies have a different amplitude.

In a nineteenth aspect, in addition to one or more of the preceding or following aspects, or in the alternative to some aspects, the control circuitry can be further configured to generate one or more electric fields with a waveform representing the superposition of at least two frequencies at least 10% different from one another.

In a twentieth aspect, in addition to one or more of the preceding or following aspects, or in the alternative to some aspects, the control circuitry can be further configured to generate one or more electric fields by stepping through one or more frequencies.

In a twenty-first aspect, in addition to one or more of the preceding or following aspects, or in the alternative to some aspects, where stepping through one or more frequencies can include a first predetermined dwell time at a first frequency.

In a twenty-second aspect, in addition to one or more of the preceding or following aspects, or in the alternative to some aspects, where the first predetermined dwell time can be in the range of 1 second to 10 hours.

In a twenty-third aspect, in addition to one or more of the preceding or following aspects, or in the alternative to some aspects, where stepping through one or more frequencies can include a second predetermined dwell time at a second frequency.

In a twenty-fourth aspect, in addition to one or more of the preceding or following aspects, or in the alternative to some aspects, where the second predetermined dwell time can be in the range of 1 second to 10 hours.

In a twenty-fifth aspect, in addition to one or more of the preceding or following aspects, or in the alternative to some aspects, where the first and second predetermined dwell times are the same.

In a twenty-sixth aspect, in addition to one or more of the preceding or following aspects, or in the alternative to some aspects, where the first and second predetermined dwell times are different.

In a twenty-seventh aspect, in addition to one or more of the preceding or following aspects, or in the alternative to some aspects, where the control circuitry can be configured to generate one or more electric fields having one or more programmable electric field strengths.

In a twenty-eighth aspect, in addition to one or more of the preceding or following aspects, or in the alternative to some aspects, where the one or more programmable electric field strengths can be selected from a range of electric field strengths between 0.25 V/cm to 1000 V/cm.

In a twenty-ninth aspect, in addition to one or more of the preceding or following aspects, or in the alternative to some aspects, where the one or more programmable electric field strengths can be selected from a range of electric field strengths between 2 V/cm to 10 V/cm.

In a thirtieth aspect, in addition to one or more of the preceding or following aspects, or in the alternative to some aspects, where the one or more programmable electric field strengths can be selected from a range of electric field strengths between 3 V/cm to 5 V/cm.

In a thirty-first aspect, in addition to one or more of the preceding or following aspects, or in the alternative to some aspects, where generating one or more electric fields comprises varying the one or more electric field strengths as a function of time.

In a thirty-second aspect, in addition to one or more of the preceding or following aspects, or in the alternative to some aspects, where generating one or more electric fields can include spatially varying one or more electric field strengths.

In a thirty-third aspect, in addition to one or more of the preceding or following aspects, or in the alternative to some aspects, where spatially varying the one or more electric field strengths can include generating a first electric field between a first pair of electrodes and generating a second electric field between a second pair of electrodes.

In a thirty-fourth aspect, in addition to one or more of the preceding or following aspects, or in the alternative to some aspects, where the first electric fields between the first pair of electrodes is stronger than the second electric field between the second pair of electrodes to achieve an equivalent electric field strength.

In a thirty-fifth aspect, in addition to one or more of the preceding or following aspects, or in the alternative to some aspects, where the control circuitry can be configured to alternate between generating electric field strengths of greater than 10 V/cm to generating electric field strengths of between 2 V/cm to 10 V/cm.

In a thirty-sixth aspect, in addition to one or more of the preceding or following aspects, or in the alternative to some aspects, where the control circuitry can be configured to generate one or more electric fields by sweeping through one or more electric field strengths.

In a thirty-seventh aspect, in addition to one or more of the preceding or following aspects, or in the alternative to some aspects, where sweeping through one or more electric field strengths can include sweeping from a first electric field strength up to a second electric field strength and sweeping from the second electric field strength down to the first electric field strength, and where the second electric field strength can be higher than the first electric field strength.

In a thirty-eighth aspect, in addition to one or more of the preceding or following aspects, or in the alternative to some aspects, where sweeping from the first electric field strength up to the second electric field strength and sweeping from the second electric field strength down to the first electric field strength can be repeated.

In a thirty-ninth aspect, in addition to one or more of the preceding or following aspects, or in the alternative to some aspects, where the one or more electric field strengths can be selected from a range of electric field strengths between 0.25 V/cm to 1000 V/cm.

In a fortieth aspect, in addition to one or more of the preceding or following aspects, or in the alternative to some aspects, where the one or more programmable electric field strengths can be selected from a range of electric field strengths between 1 V/cm to 10 V/cm.

In a forty-first aspect, in addition to one or more of the preceding or following aspects, or in the alternative to some aspects, where the control circuitry can be further configured to generate one or more electric fields by using a voltage control mode, the voltage control mode including modulating voltage in order to result in a desired electric field strength.

In a forty-second aspect, in addition to one or more of the preceding or following aspects, or in the alternative to some aspects, where the control circuitry can be configured to record electric field strength over time.

In a forty-third aspect, in addition to one or more of the preceding or following aspects, or in the alternative to some aspects, where the control circuitry can be configured to generate one or more electric fields by using a current control mode, where the current control mode can include modulating current in order to result in a desired electric field strength.

In a forty-fourth aspect, in addition to one or more of the preceding or following aspects, or in the alternative to some aspects, where the control circuit can be further configured to adjust the current to maintain a substantially constant electric field strength.

In a forty-fifth aspect, in addition to one or more of the preceding or following aspects, or in the alternative to some aspects, where the control circuitry can be further configured to record electric field strength and at least one of voltage and current at a plurality of time points.

In a forty-sixth aspect, in addition to one or more of the preceding or following aspects, or in the alternative to some aspects, where the control circuitry can be configured to generate one or more electric fields by implementing one or more duty cycles.

In a forty-seventh aspect, in addition to one or more of the preceding or following aspects, or in the alternative to some aspects, where implementing one or more duty cycles can include generating one or more electric fields at a constant frequency for a predetermined ON time period, followed by a predetermined OFF time period.

In a forty-eighth aspect, in addition to one or more of the preceding or following aspects, or in the alternative to some aspects, where the predetermined ON time period can be selected from a range between 4 hours to 18 hours, and the predetermined OFF time period can be selected from a range between 6 hours to 20 hours.

In a forty-ninth aspect, in addition to one or more of the preceding or following aspects, or in the alternative to some aspects, where implementing one or more duty cycles can include generating one or more electric fields at a constant electric field strength for a predetermined ON time period, followed by a predetermined OFF time period.

In a fiftieth aspect, in addition to one or more of the preceding or following aspects, or in the alternative to some aspects, where the predetermined ON time period can be selected from a range between 4 hours to 18 hours, and the predetermined OFF time period can be selected from a range between 6 hours to 20 hours.

In a fifty-first aspect, in addition to one or more of the preceding or following aspects, or in the alternative to some aspects, where the control circuitry can be configured to generate one or more electric fields having an electrical waveform alternating between positive pulses and negative pulses, where the waveform can include one or more OFF time periods between at least some adjacent positive and negative pulses.

In a fifty-second aspect, in addition to one or more of the preceding or following aspects, or in the alternative to some aspects, where the positive pulses and negative pulses can be relative to a bias voltage.

In a fifty-third aspect, in addition to one or more of the preceding or following aspects, or in the alternative to some aspects, where the OFF time periods can be defined by an electrical potential equal to the bias voltage.

In a fifty-fourth aspect, in addition to one or more of the preceding or following aspects, or in the alternative to some aspects, where the bias voltage can be from −5 V to 5 V.

In a fifty-fifth aspect, in addition to one or more of the preceding or following aspects, or in the alternative to some aspects, where the bias voltage can be 0 V.

In a fifty-sixth aspect, in addition to one or more of the preceding or following aspects, or in the alternative to some aspects, where the control circuitry can be further configured to generate one or more electric fields by delivering one or more electrical pulses with a biphasic waveform.

In a fifty-seventh aspect, in addition to one or more of the preceding or following aspects, or in the alternative to some aspects, the biphasic electrical waveform can include one positive pulse followed by one negative pulse.

In a fifty-eighth aspect, in addition to one or more of the preceding or following aspects, or in the alternative to some aspects, the biphasic electrical waveform can include two positive pulses followed by two negative pulses.

In a fifty-ninth aspect, in addition to one or more of the preceding or following aspects, or in the alternative to some aspects, the electrical waveform can include one or more of a square waveform, a triangular waveform, a sinusoidal waveform, or a capacitive decay waveform.

In a sixtieth aspect, in addition to one or more of the preceding or following aspects, or in the alternative to some aspects, the electrical waveform can include more than one of a square waveform, a triangular waveform, a sinusoidal waveform, or a capacitive decay waveform.

In a sixty-first aspect, in addition to one or more of the preceding or following aspects, or in the alternative to some aspects, the electrical waveform can alternate between a first waveform selected from the group consisting of a square waveform, a triangular waveform, a sinusoidal waveform, or a capacitive decay waveform and a second waveform selected from the group consisting of a square waveform, a triangular waveform, a sinusoidal waveform, or a capacitive decay waveform; wherein the first waveform and the second waveform are different.

In a sixty-second aspect, in addition to one or more of the preceding or following aspects, or in the alternative to some aspects, where the control circuitry can be configured to generate one or more electric fields having an electrical waveform including a sequence of positive pulses, negative pulses, and OFF time periods, the electrical waveform including at least one of two positive pulses separated by an OFF time period but not a negative phase, or two negative pulses separated by an OFF time period but not a positive phase.

In a sixty-third aspect, in addition to one or more of the preceding or following aspects, or in the alternative to some aspects, where the positive pulses and negative pulses can be relative to a bias voltage.

In a sixty-fourth aspect, in addition to one or more of the preceding or following aspects, or in the alternative to some aspects, where the OFF time periods can be defined by an electrical potential equal to the bias voltage.

In a sixty-fifth aspect, in addition to one or more of the preceding or following aspects, or in the alternative to some aspects, where the bias voltage can be from –5 V to 5 V.

In a sixty-sixth aspect, in addition to one or more of the preceding or following aspects, or in the alternative to some aspects, where the bias voltage can be 0 V.

In a sixty-seventh aspect, in addition to one or more of the preceding or following aspects, or in the alternative to some aspects, where the control circuitry can be configured to periodically generate one or more electric fields at frequencies greater than 1 MHz.

In a sixty-eighth aspect, in addition to one or more of the preceding or following aspects, or in the alternative to some aspects, where generating one or more electric fields at frequencies greater than 1 MHz can be of a magnitude sufficient to cause tissue heating.

In a sixty-ninth aspect, in addition to one or more of the preceding or following aspects, or in the alternative to some aspects, where the control circuitry can be configured to periodically generate one or more electric fields at an electric field strength in a target tissue sufficient to cause electroporation and subsequent cell death.

In a seventieth aspect, in addition to one or more of the preceding or following aspects, or in the alternative to some aspects, where the field strength is greater than 1000V/cm.

In a seventy-first aspect, in addition to one or more of the preceding or following aspects, or in the alternative to some aspects, a medical device is included. The medical device can include an electric field generating circuit configured to generate one or more electric fields and control circuitry in communication with the electric field generating circuit. The control circuitry can be configured to control delivery of the one or more electric fields from the electric field generating circuit. The medical device can include one or more leads in electrical communication with the electric field generating circuit. The control circuitry can cause the electric field generating circuit to generate one or more electric fields at frequencies selected from a range of between 10 kHz to 1 MHz at the site of a cancerous tumor located within a bodily tissue.

In a seventy-second aspect, in addition to one or more of the preceding or following aspects, or in the alternative to some aspects, the one or more leads can include one or more circular leads.

In a seventy-third aspect, in addition to one or more of the preceding or following aspects, or in the alternative to some aspects, where the one or more circular leads can include one or more electrodes disposed about its circumference.

In a seventy-fourth aspect, in addition to one or more of the preceding or following aspects, or in the alternative to some aspects, where the one or more electrodes can include one or more electrode pairs disposed about the circumference of the one or more circular leads such that sequentially generate one or more electric fields at the one or more electrode pairs to generate corresponding electric fields.

In a seventy-fifth aspect, in addition to one or more of the preceding or following aspects, or in the alternative to some aspects, where sequentially generating one or more electric fields at the one or more electrode pairs generates a three-dimensional electric field about the one or more circular leads.

In a seventy-sixth aspect, in addition to one or more of the preceding or following aspects, or in the alternative to some aspects, the one or more leads can include three or more electrodes comprising a plurality of electric field vectors disposed circumferentially about an axis of field rotation.

In a seventy-seventh aspect, in addition to one or more of the preceding or following aspects, or in the alternative to some aspects, where the control circuitry can be configured to create an electric field that effectively rotates via the plurality of electric field vectors disposed circumferentially about an axis of field rotation.

In a seventy-eighth aspect, in addition to one or more of the preceding or following aspects, or in the alternative to some aspects, where the electric field can be generated by sequentially varying the electric field at one or more vectors disposed circumferentially about an axis of field rotation.

In a seventy-ninth aspect, in addition to one or more of the preceding or following aspects, or in the alternative to some aspects, where the electric field can be generated by sequentially generating more than one electric field between one master electrode paired to one or more additional electrodes disposed circumferentially about the axis of field rotation.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which:

FIG. 26 is a plot of an exemplary therapy parameter in accordance with various embodiments herein.

FIG. 27 is a plot of an exemplary therapy parameter in accordance with various embodiments herein.

FIG. 28 is a plot of an exemplary therapy parameter in accordance with various embodiments herein.

FIG. 29 is a plot of an exemplary therapy parameter in accordance with various embodiments herein.

FIG. 30 is a plot of an exemplary therapy parameter in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few.

While not intending to be bound by theory, it is believed that alternating electric fields can disrupt mitosis within a cancerous tumor by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances an alternating electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules, can result in apoptosis (i.e., programmed cell death).

It is also believed that alternating electric fields can lead to increased electric field density near the cleavage furrow of the dividing cells during telophase. An increased electric field density in the region of the cleavage furrow can result in dielectrophoresis of charged macromolecules, such as proteins and nucleic acids, toward the high electric field density at the furrow. The unequal concentration of key macromolecules required for cellular division at the site of the cleavage furrow can disrupt the final separation of the sister cells during telophase and eventually lead to apoptosis.

Figures 1, 2:
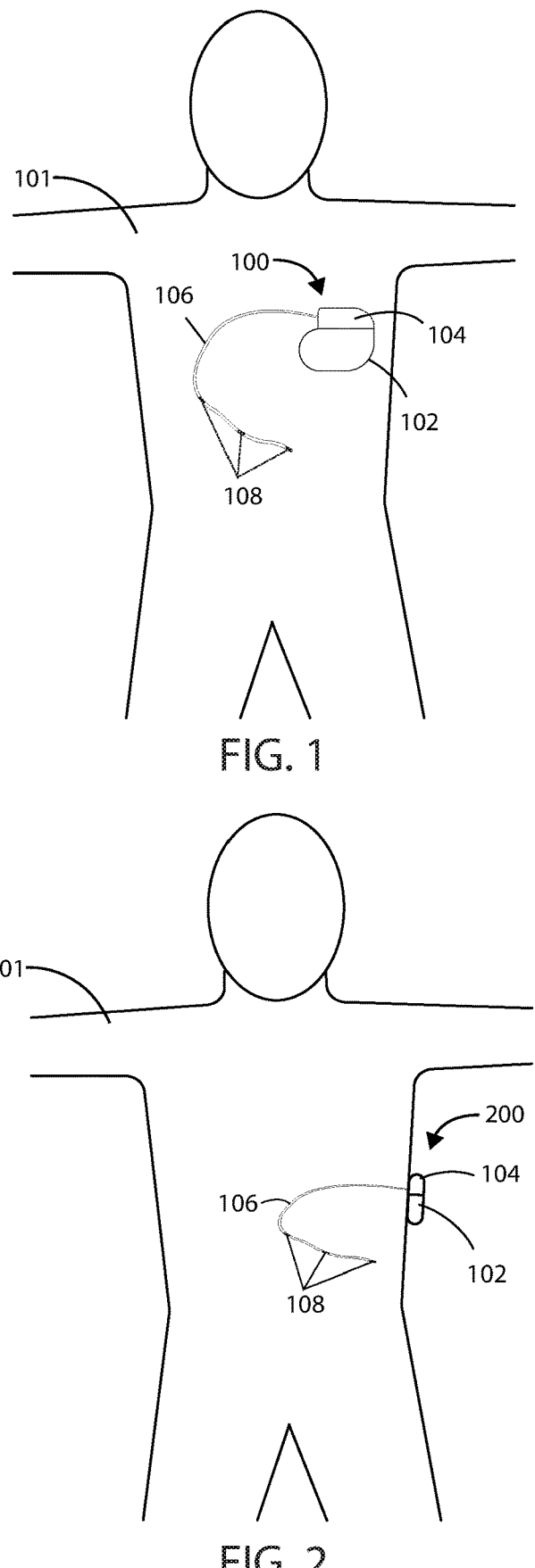
FIG. 1 is a schematic view of a medical system in accordance with various embodiments herein.
FIG. 2 is a schematic view of a medical system in accordance with various embodiments herein.

Referring now to FIG. 1, a schematic view is shown of a medical device 100 in accordance with various embodiments herein. The medical device 100 can be implanted entirely within the body of a patient 101 at or near the site of a cancerous tumor located within a bodily tissue. Various implant sites can be used including areas such as in the limbs, the upper torso, the abdominal area, the head, and the like.

Referring now to FIG. 2, another schematic view is shown of a medical device 200 in accordance with various embodiments herein. The medical device 200 can be partially implanted within the body of a patient 101. In some embodiments, the medical device can be partially implanted and partially external to the body of a patient. In other embodiments, a partially implanted medical device can include a transcutaneous connection between components disposed internal to the body and external to the body.

Implanted medical device 100 and partially implanted medical device 200 can wirelessly communicate patient identification data, diagnostic information, electric field data, physiological parameters, software updates, and the like with a fully or partially external portion of a medical device over a wireless connection. Implanted medical device 100 and partially implanted medical device 200 can also wirelessly communicate with an external device configured to wirelessly charge the medical device utilizing inductance, radio frequency, and acoustic energy transfer techniques, and the like.

In some embodiments, a portion of the medical device can be entirely implanted and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include the many of the same components as and can be configured to perform many of the same functions as a pulse generator. In embodiments where a portion of a medical device is entirely implanted and a portion of the medical device is entirely external, the portion of the medical device that is entirely external can communicate wirelessly with the portion of the medical device that is entirely internal. However, in other embodiments a wired connection can be used.

The medical device 100 or medical device 200 can include a housing 102 and a header 104 coupled to the housing 102. Various materials can be used. However, in some embodiments, the housing 102 can be formed of a material such as a metal, ceramic, polymer, composite, or the like. In some embodiments, the housing 102, or one or more portions thereof, can be formed of titanium. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow.

In some embodiments where a portion of the medical device 100 or 200 is partially external, the header 104 and housing 102 can be surrounded by a protective casing made of durable polymeric material. In other embodiments, where a portion of the medical device 100 or 200 is partially external, the header 104 and housing 102 can be surrounded by a protective casing made of a combination of polymeric material, metallic material, and/or glass material.

The header 104 can be coupled to one or more leads 106. The header 104 can serve to provide fixation of the proximal end of one or more leads 106 and electrically couple the one or more leads 106 to one or more components within the housing 102. The one or more leads 106 can include one or more electrodes 108 disposed along the length of the electrical leads 106. In some embodiments, electrodes 108 can include electric field generating electrodes and in other embodiments electrodes 108 can include electric field sensing electrodes. In some embodiments, leads 106 can include both electric field generating and electric field sensing electrodes. In other embodiments, leads 106 can include any number of electrodes that are both electric field sensing and electric field generating. It will be appreciated that while many embodiments of medical devices herein are designed to function with leads, leadless medical devices that generate electrical fields are also contemplated herein.

Figure 3:
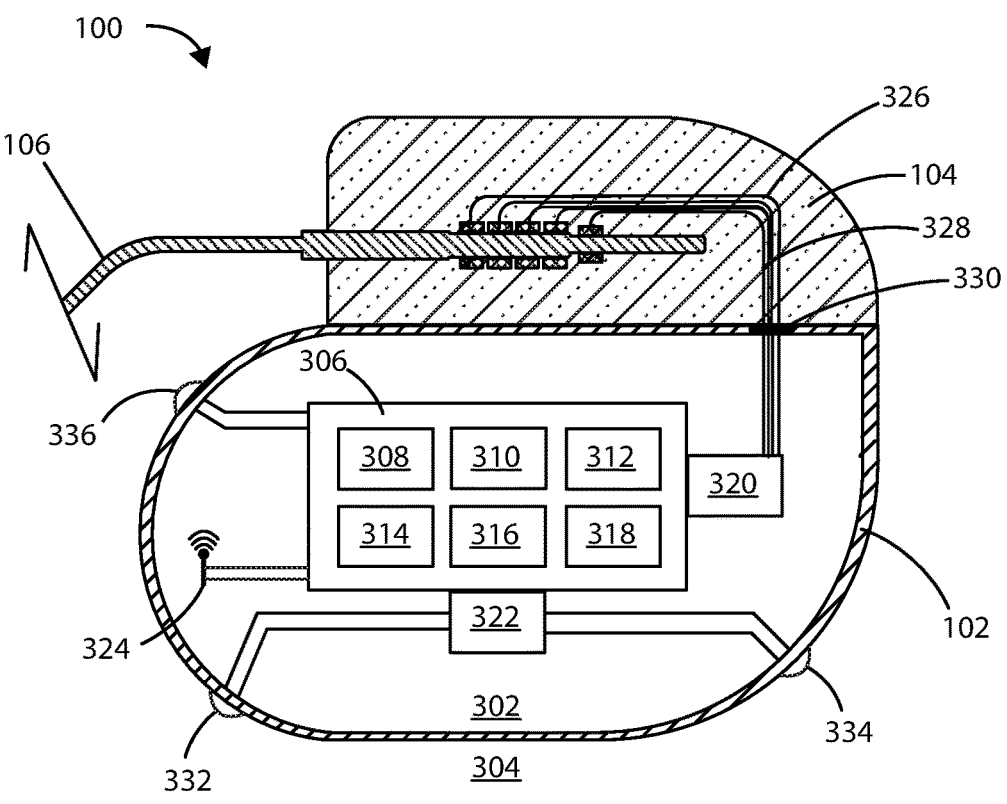
FIG. 3 is a schematic cross-sectional view of a medical device in accordance with various embodiments herein.

Referring now to FIG. 3, a schematic cross-sectional view of medical device 100 is shown in accordance with various embodiments herein. Housing 102 can define an interior volume 302 that can be hollow and that in some embodiments is hermetically sealed off from the area 304 outside of medical device 100. In other embodiments the housing 102 can be filled with components and/or structural materials such that it is non-hollow. The medical device 100 can include control circuitry 306, which can include various components 308, 310, 312, 314, 316, and 318 disposed within housing 102. In some embodiments, these components can be integrated and in other embodiments these components can be separate. In yet other embodiments, there can be a combination of both integrated and separate components. The medical device 100 can also include an antenna 324, to allow for unidirectional or bidirectional wireless data communication. In some embodiments, the components of medical device 100 can include an inductive energy receiver coil (not shown) communicatively coupled or attached thereto to facilitate transcutaneous recharging of the medical device via recharging circuitry.

The various components 308, 310, 312, 314, 316, and 318 of control circuitry 306 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 306 can be in communication with an electric field generating circuit 320 that can be configured to generate electric current to create one or more fields. The electric field generating circuit 320 can be integrated with the control circuitry 306 or can be a separate component from control circuitry 306. Control circuitry 306 can be configured to control delivery of electric current from the electric field generating circuit 320. In some embodiments, the electric field generating circuit 320 can be present in a portion of the medical device that is external to the body.

In some embodiments, the control circuitry 306 can be configured to direct the electric field generating circuit 320 to deliver an electric field using one or more frequencies selected from a range of between 10 kHz to 1 MHz. In some embodiments, the control circuitry 306 can be configured to direct the electric field generating circuit 320 to deliver an electric field at one or more frequencies selected from a range of between 100 kHz to 500 kHz. In some embodiments, the control circuitry 306 can be configured to direct the electric field generating circuit 320 to deliver an electric field at one or more frequencies selected from a range of between 100 kHz to 300 kHz. In some embodiments, the control circuitry 306 can be configured to direct the electric field generating circuit 320 to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry 306 can be configured to direct the electric field generating circuit 320 to deliver an electric field using currents ranging from 1 mAmp to 1000 mAmp to the site of a cancerous tumor. In some embodiments, the control circuitry 306 can be configured to direct the electric field generating circuit 320 to deliver an electric field using currents ranging from 20 mAmp to 500 mAmp to the site of a cancerous tumor. In some embodiments, the control circuitry 306 can be configured to direct the electric field generating circuit 320 to deliver an electric field using currents ranging from 30 mAmp to 300 mAmp to the site of a cancerous tumor.

In some embodiments, the control circuitry 306 can be configured to direct the electric field generating circuit 320 to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 320 to deliver an electric field at a current falling within a range, wherein any of the forgoing currents can serve as the lower or upper bound of the range, provided that the lower bound of the range is a value less than the upper bound of the range.

In some embodiments, the control circuitry 306 can be configured to direct the electric field generating circuit 320 to deliver an electric field using voltages ranging from 1 V$_{rms}$ to 50 V$_{rms}$ to the site of a cancerous tumor. In some embodiments, the control circuitry 306 can be configured to direct the electric field generating circuit 320 to deliver an electric field using voltages ranging from 5 V$_{rms}$ to 30 V$_{rms}$ to the site of a cancerous tumor. In some embodiments, the control circuitry 306 can be configured to direct the electric field generating circuit 320 to deliver an electric field using voltages ranging from 10 V$_{rms}$ to 20 V$_{rms}$ to the site of a cancerous tumor.

In some embodiments, the control circuitry 306 can be configured to direct the electric field generating circuit 320 to deliver an electric field using one or more voltages including 1 V$_{rms}$, 2 V$_{rms}$, 3 V$_{rms}$, 4 V$_{rms}$, 5 V$_{rms}$, 6 V$_{rms}$, 7 V$_{rms}$, 8 V$_{rms}$, 9 V$_{rms}$, 10 V$_{rms}$, 15 V$_{rms}$, 20 V$_{rms}$, 25 V$_{rms}$, 30 V$_{rms}$, 35 V$_{rms}$, 40 V$_{rms}$, 45 V$_{rms}$, or 50 V. It will be appreciated that the control circuitry can be configured to direct the electric field generating circuit 320 to deliver an electric field using a voltage falling within a range, wherein any of the forgoing voltages can serve as the lower or upper bound of the range, provided that the lower bound of the range is a value less than the upper bound of the range.

In some embodiments, the control circuitry 306 can be configured to direct the electric field generating circuit 320 to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit 320 can deliver an electric field using a frequency falling within a range, wherein any of the foregoing frequencies can serve as the upper or lower bound of the range, provided that the upper bound is greater than the lower bound.

In some embodiments, the control circuitry 306 can be configured to direct the electric field generating circuit 320 to generate one or more applied electric field strengths selected from a range of between 0.25 V/cm to 1000 V/cm. In some embodiments, the control circuitry 306 can be configured to direct the electric field generating circuit 320 to generate one or more applied electric field strengths of greater than 3 V/cm. In some embodiments, the control circuitry 306 can be configured to direct the electric field generating circuit 320 to generate one or more applied electric field strengths selected from a range of between 1 V/cm to 10 V/cm. In some embodiments, the control circuitry 306 can be configured to direct the electric field generating circuit 320 to generate one or more applied electric field strengths selected from a range of between 3 V/cm to 5 V/cm.

In other embodiments, the control circuitry 306 can be configured to direct the electric field generating circuit 320 to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0

V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit 320 can generate an electric field having a field strength at a treatment site falling within a range, wherein any of the foregoing field strengths can serve as the upper or lower bound of the range, provided that the upper bound is greater than the lower bound.

In some embodiments, the control circuitry 306 can be configured to direct the electric field generating circuit 320 to deliver an electric field via leads 106 to the site of a cancerous tumor located within a bodily tissue. In other embodiments, the control circuitry 306 can be configured to direct the electric field generating circuit 320 to deliver an electric field via the housing 102 of medical device 100 to the site of a cancerous tumor located within a bodily tissue. In other embodiments, the control circuitry 306 can be configured to direct the electric field generating circuit 320 to deliver an electric field between leads 106 and the housing 102 of medical device 100. In some embodiments, one or more leads 106 can be in electrical communication with the electric field generating circuit 320. In some embodiments, the one or more leads 106 can include one or more electrodes 108 disposed along the length of the leads 106, where the electrodes 108 can be in electrical communication with the electric field generating circuit 320.

In some embodiments, various components within medical device 100 can include an electric field sensing circuit 322 configured to generate a signal corresponding to sensed electric fields. Electric field sensing circuit 322 can be integrated with control circuitry 306 or it can be separate from control circuitry 306.

Sensing electrodes can be disposed on or adjacent to the housing of the medical device, on one or more leads connected to the housing, on a separate device implanted near or in the tumor, or any combination of these locations. In some embodiments, the electric field sensing circuit 322 can include a first sensing electrode 332 and a second sensing electrode 334. In other embodiments, the housing 102 itself can serve as a sensing electrode for the electric field sensing circuit 322. The electrodes 332 and 334 can be in communication with the electric field sensing circuit 322. The electric field sensing circuit 322 can measure the electrical potential difference (voltage) between the first electrode 332 and the second electrode 334. In some embodiments, the electric field sensing circuit 322 can measure the electrical potential difference (voltage) between the first electrode 332 or second electrode 334, and an electrode disposed along the length of one or more leads 106. In some embodiments, the electric field sensing circuit can be configured to measure sensed electric fields and to record electric field strength in V/cm.

It will be appreciated that the electric field sensing circuit 322 can additionally measure an electrical potential difference between the first electrode 332 or the second electrode 334 and the housing 102 itself. In other embodiments, the medical device can include a third electrode 336, which can be an electric field sensing electrode or an electric field generating electrode. In some embodiments, one or more sensing electrodes can be disposed along lead 106 and can serve as additional locations for sensing an electric field. Many combinations can be imagined for measuring electrical potential difference between electrodes disposed along the length of one or more leads 106 and the housing 102 in accordance with the embodiments herein.

In some embodiments, the one or more leads 106 can be in electrical communication with the electric field generating circuit 320. The one or more leads 106 can include one or more electrodes 108, as shown in FIGS. 1 and 2. In some embodiments, various electrical conductors, such as electrical conductors 326 and 328, can pass from the header 104 through a feed-through structure 330 and into the interior volume 302 of medical device 100. As such, the electrical conductors 326 and 328 can serve to provide electrical communication between the one or more leads 106 and control circuitry 306 disposed within the interior volume 302 of the housing 102.

In some embodiments, recorder circuitry can be configured to record the data produced by the electric field sensing circuit 322 and record time stamps regarding the same. In some embodiments, the control circuitry 306 can be hardwired to execute various functions, while in other embodiments the control circuitry 306 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 4:
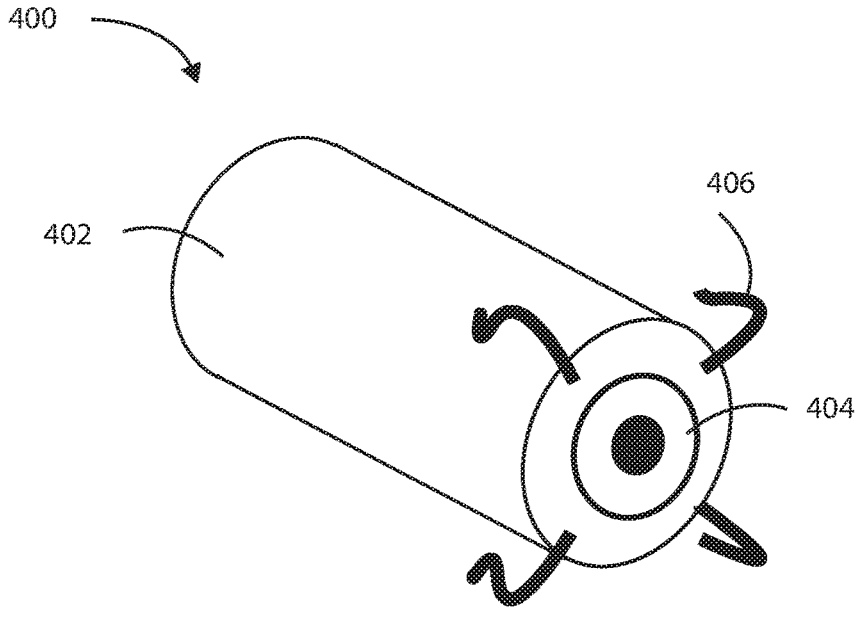
FIG. 4 is a schematic view of a medical device in accordance with various embodiments herein.

Referring now to FIG. 4, leadless medical device 400 is shown in accordance with the embodiments herein. The leadless medical device 400 can include a housing 402 and a header 404 coupled to the housing 402. Various materials can be used. However, in some embodiments, the housing 402 can be formed of a material such as a metal, ceramic, polymer, composite, or the like. In some embodiments, the housing 402, or one or more portions thereof, can be formed of titanium. The header 404 can be formed of various materials, but in some embodiments the header 404 can be formed of a translucent polymer such as an epoxy material. In some embodiments the header 404 can be hollow. In other embodiments the header 404 can be filled with components and/or structural materials such as epoxy or another material such that it is non-hollow. In some embodiments, leadless medical device 400 can include fixation elements 406 to keep a leadless medical device 400 positioned at or near the site of a cancerous tumor within the body. In some embodiments, fixation elements 406 can include talons, tines, helices, bias, and the like.

Figure 5:
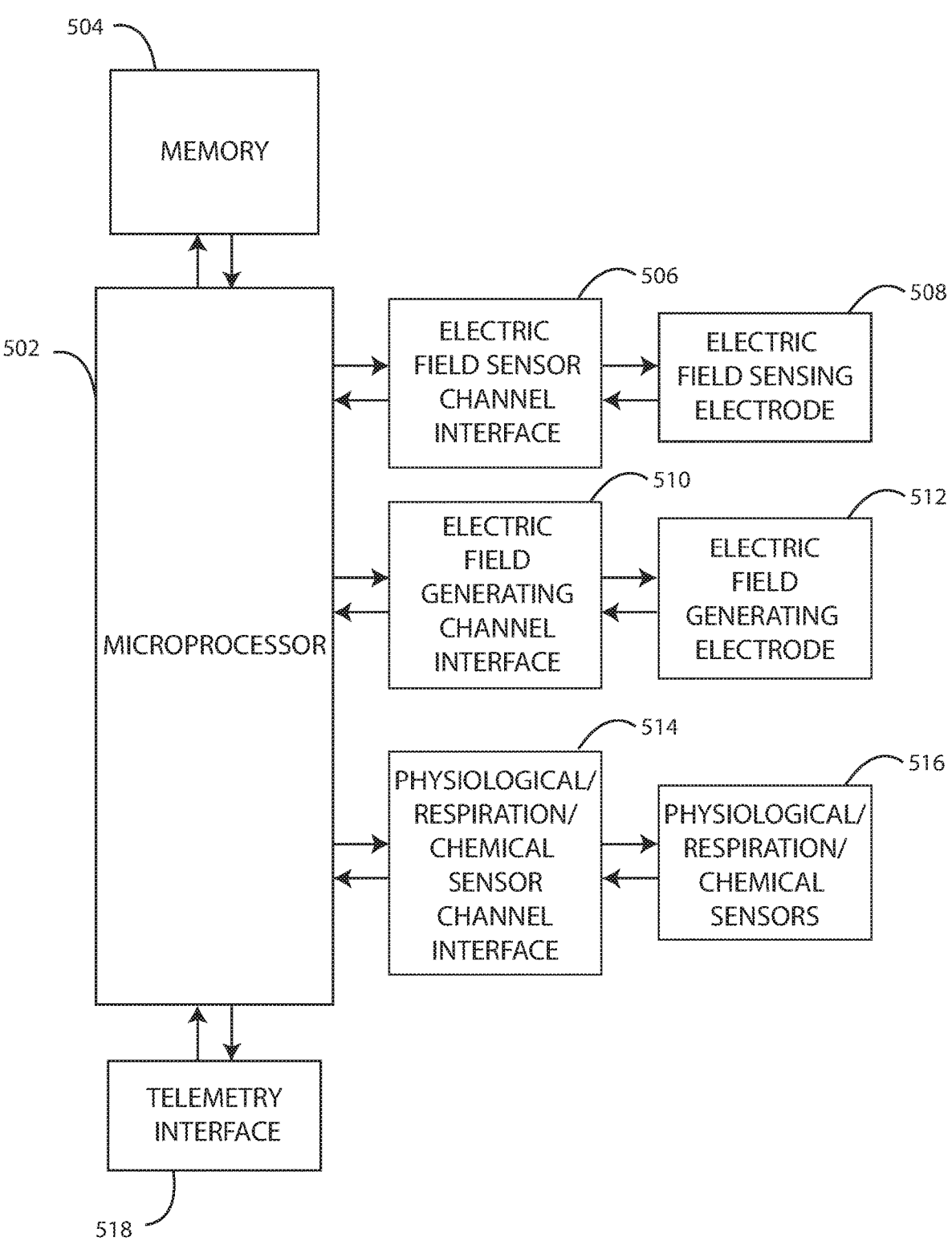
FIG. 5 is a schematic diagram of components of a medical device in accordance with various embodiments herein.

Elements of various embodiments of the medical devices described herein are shown in FIG. 5. However, it will be appreciated that some embodiments can include additional elements beyond those shown in FIG. 5. In addition, some embodiments may lack some elements shown in FIG. 5. The medical devices as embodied herein can gather information through one or more sensing channels and can output information through one or more field generating channels. A microprocessor 502 can communicate with a memory 504 via a bidirectional data bus. The memory 504 can include read only memory (ROM) or random access memory (RAM) for program storage and RAM for data storage. The microprocessor 502 can also be connected to a telemetry interface 518 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. In some embodiments, the medical device can include an inductive energy receiver coil interface (not shown) communicatively coupled or attached thereto to facilitate transcutaneous recharging of the medical device. In some embodiments, the medical device can include a receiving transducer configured to be communicatively coupled with an external transmitter so that the medical device can be wirelessly charged by acoustic energy transfer technology. In some embodiments, the medical device can include a radio frequency receiver configured to receive radio frequency energy and convert it into DC power used to wirelessly charge the medical device.

The medical device can include one or more electric field sensing electrodes 508 and one or more electric field sensor channel interfaces 506 that can communicate with a port of microprocessor 502. The medical device can also include one or more electric field generating electrodes 512 and one or more electric field generating channel interfaces 510 that can communicate with a port of microprocessor 502. The medical device can also include one or more physiological sensors, respiration sensors, or chemical sensors 516 and one or more physiological/respiration/chemical sensor channel interfaces 514 that can communicate with a port of microprocessor 502. The channel interfaces 506, 510, and 514 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the physiological sensors can include sensors that monitor temperature, blood flow, blood pressure, and the like. In some embodiments, the respiration sensors can include sensors that monitor respiration rate, respiration peak amplitude, and the like. In some embodiments, the chemical sensors can measure the quantity of an analyte present in a treatment area about the sensor, including but not limited to analytes such as of blood urea nitrogen, creatinine, fibrin, fibrinogen, immunoglobulins, deoxyribonucleic acids, ribonucleic acids, potassium, sodium, chloride, calcium, magnesium, lithium, hydronium, hydrogen phosphate, bicarbonate, and the like. However, many other analytes are also contemplated herein. Exemplary chemical/analyte sensors are disclosed in commonly owned U.S. Pat. No. 7,809,441 to Kane et al., and which is hereby incorporated by reference in its entirety.

Although the physiological, respiration, or chemical sensors 516 are shown as part of a medical device in FIG. 5, it is realized that in some embodiments one or more of the physiological, respiration, or chemical sensors could be physically separate from the medical device. In various embodiments, one or more of the physiological, respiration, or chemical sensors can be within another implanted medical device communicatively coupled to a medical device via telemetry interface 518. In yet other embodiments, one or more of the physiological, respiration, or chemical sensors can be external to the body and coupled to a medical device via telemetry interface 518.

Figure 6:
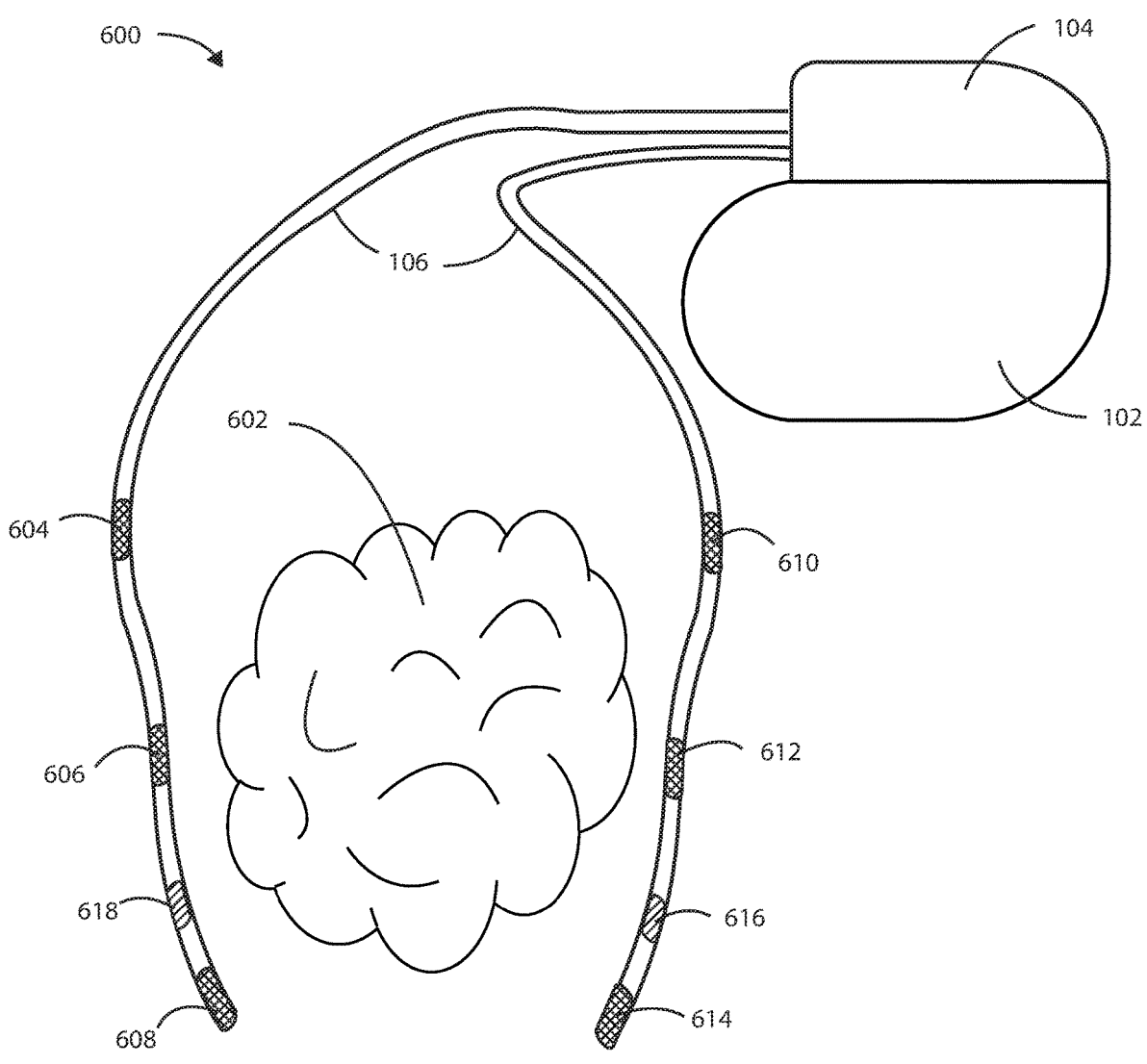
FIG. 6 is a schematic view of a medical device in accordance with various embodiments herein.

Referring now to FIG. 6, a schematic diagram of a medical device 600 is shown in accordance with the embodiments herein. Medical device 600 can include housing 102 and header 104, and one or more leads 106. Leads 106 can include one or more electrodes such as electrodes 604, 606, 608, 610, 612, or 614 disposed along the length of the leads 106. In some embodiments, electrodes 604, 606, 608, 610, 612, or 614 can include electric field generating electrodes and in other embodiments electrodes 604, 606, 608, 610, 612, or 614 can include electric field sensing electrodes. In some embodiments, leads 106 can include both electric field generating and electric field sensing electrodes.

The proximal ends of leads 106 are disposed within the header 104. The distal ends of electrical leads 106 can surround a cancerous tumor 602 such that the electrodes 604, 606, 608, 610, 612, or 614 are brought into proximity of the cancerous tumor 602. In some embodiments, the leads 106 can be positioned within the vasculature such that electrodes 604, 606, 608, 610, 612, or 614 are adjacent to or positioned within the cancerous tumor 602. However, it will be appreciated that leads 106 can be disposed in various places within or around the cancerous tumor 602. In some embodiments, the leads 106 can pass directly through the cancerous tumor 602.

In some embodiments, the leads 106 can include one or more tracking markers 616 or 618 along the length of the lead for use in determining the precise location of the electrodes relative to the tumor. In some embodiments, the one or more tracking markers can be disposed directly distal or directly proximal to the one or more electrodes disposed on the lead. In some embodiments, the tracking markers can be formed from a magnetic material. In some embodiments, the tracking markers can be formed from a radiographic material. In some embodiments, the tracking markers can be formed from a fluorographic material.

It will be appreciated that a plurality of electric field vectors can be generated between various combinations of electrodes 604, 606, 608, 610, 612, or 614 disposed along leads 106 to create an electric field. For example, one or more electric field vectors can be generated between electrodes 604 and 610. Similarly, one or more electric field vectors can be generated between electrodes 606 and 612. It will also be appreciated that one or more electric field vectors can be generated between any combination of electrodes 604, 606, 608, 610, 612, or 614. In some embodiments, one or more electric field vectors can be generated between any combination of electrodes 604, 606, 608, 610, 612, or 614 and the housing 102 of medical device 400. It will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

Therapy Parameters

Successful treatment of cancerous tumors can depend on a number of variables, including electric field strength, frequency, cell heterogeneity, cell size, cancer cell type, tumor size, and location within the body. A variety of therapy parameters can be implemented using the medical devices described herein. One or more therapeutic parameter sets can be programmed into the memory of the medical devices and implemented by the control circuitry 306, shown in FIG. 3. Exemplary therapeutic parameter sets can include those that implement the following concepts: sweeping through a range of frequencies; stacking of one or more frequencies simultaneously; stepping through one or more frequencies sequentially; the spatial or temporal delivery of one or more electric fields; sweeping through a range of electric field strengths; applying an effective rotating electric field; modulating a voltage control mode or a current control mode; implementing one or more duty cycles; pulse width modulation; manipulation of the electrical waveform shape and/or pulse sequence; and the occasional use of high frequency or high electric fields strength pulses.

The therapeutic parameter sets can be programmed into a medical device to operate autonomously, or they can be queried and manipulated by the patient or a clinician using an external computation device such as a programmer, a home-based unit, and/or a mobile unit (e.g. a cellular phone, personal computer, smart phone, tablet computer, and the like). In other embodiments, the therapeutic parameter sets can be wirelessly communicated to the medical device from an external computation device. Frequencies and/or electric field strengths suitable for use in any of the therapeutic parameter sets herein are discussed above with respect to electric field generating circuit 320. In some embodiments, one or more therapeutic parameter sets can be implemented simultaneously. In other embodiments, one or more therapeutic parameter sets can be implemented in an alternating fashion. Therapeutic parameter sets suitable for use with the medical devices embodied herein will be discussed below in reference to FIGS. 7-30.

Frequency Sweep

Figure 7:
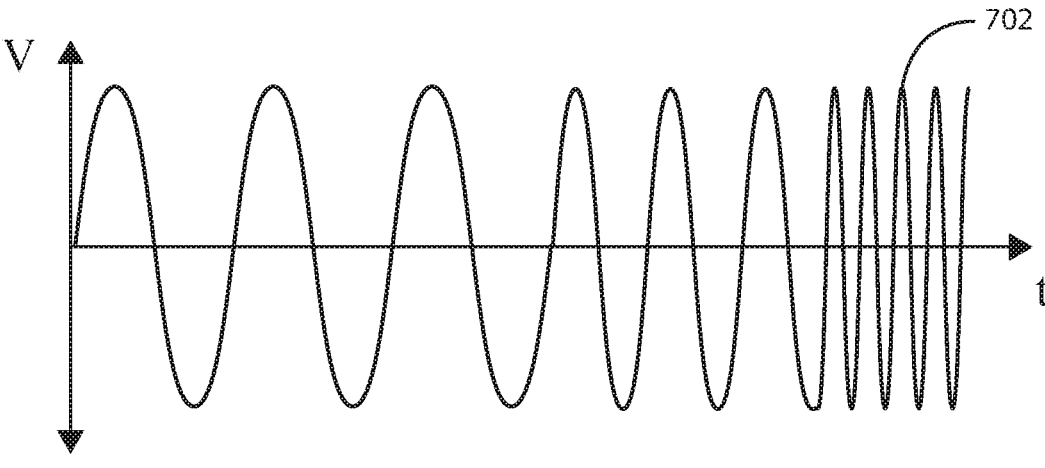
FIG. 7 is a plot of an exemplary therapy parameter in accordance with various embodiments herein.
Figure 8:
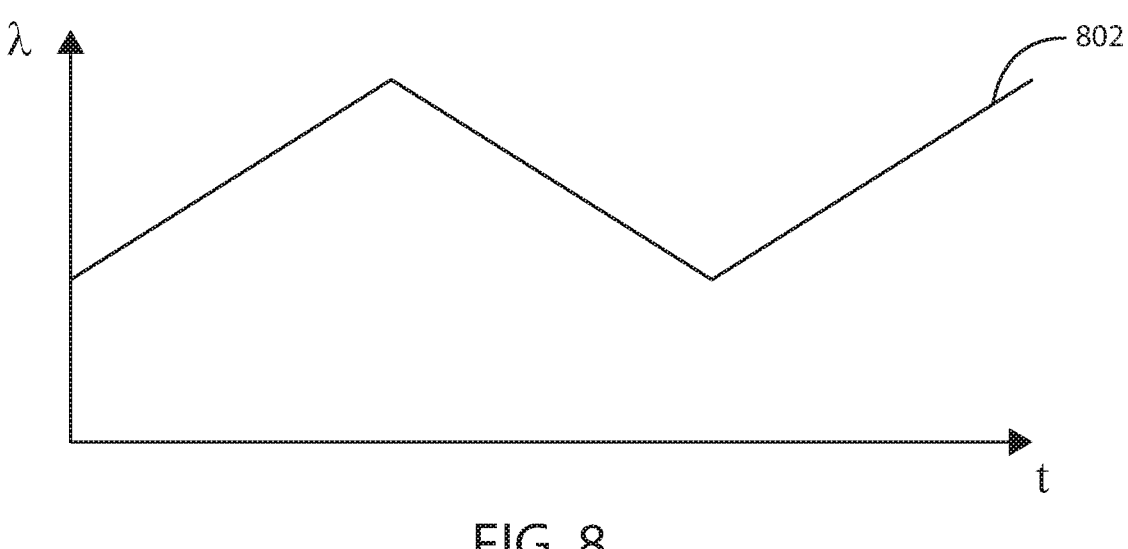
FIG. 8 is a plot of an exemplary therapy parameter in accordance with various embodiments herein.

In some embodiments, an electric field can be applied to the site of a cancerous tumor by sweeping through a range of frequencies. Referring now to FIG. 7, exemplary plot 702 shows an alternating electric field, where the frequency of the increases over time. Similarly, FIG. 8 shows the change in frequency as a function of time in exemplary plot 802 during a programmed therapy parameter. In some embodiments, a frequency sweep can include sweeping from a minimum frequency up to a maximum frequency. In some embodiments, a frequency sweep can include sweeping from a maximum frequency down to a minimum frequency. In other embodiments, sweeping from a minimum frequency up to a maximum frequency and sweeping from the maximum frequency down to the minimum frequency can be repeated as many times as desired throughout the duration of the delivery of the electric field from the electric field generating circuit.

As therapy progresses during a frequency sweep, it may be desired to alternate between frequency ranges so that as the cells within a population change in size and number in response to therapy, more cells can be targeted. For example, in some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy. In some embodiments, the second frequency sweep (range) can be at higher frequencies than the first frequency sweep (range). In some embodiments, the first frequency sweep (range) can be at higher frequencies than the second frequency sweep (range).

Frequency ranges for the first and second frequency ranges can be any range including specific frequencies recited above with respect to electric field generating circuit 220, provided that the lower end of each range is a value less than the upper end of each range. At times, it may be beneficial to have some amount of overlap between the frequency range of the first and second frequency sweep.

Stacked Frequencies

Figure 9:
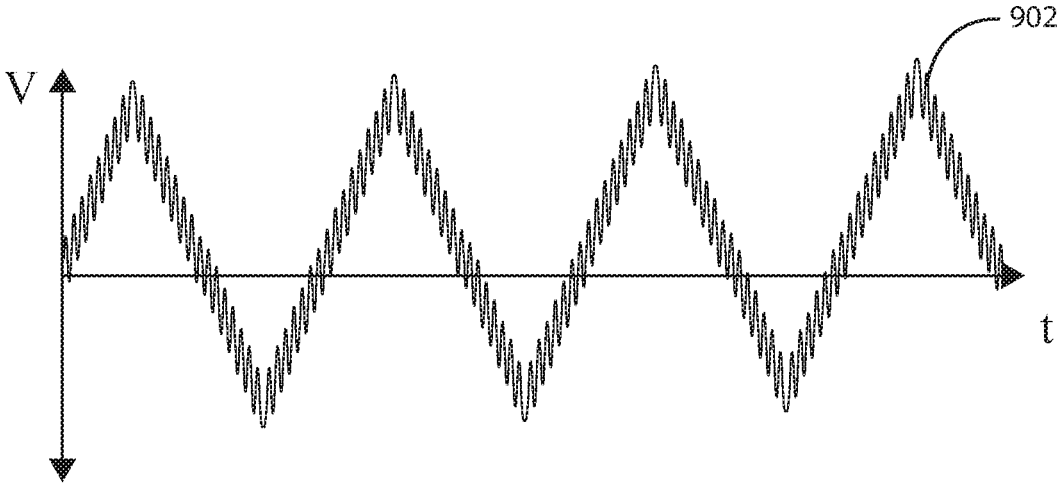
FIG. 9 is a plot of an exemplary therapy parameter in accordance with various embodiments herein.

In some embodiments, it may be advantageous to deliver a stack of one or more frequencies simultaneously to the site of a cancerous tumor. Without intending to be bound by theory, it is believed that stacking one or more frequencies can create a stronger and more robust electric field allowing for a more effective treatment for a range of cell types and tumor locations. In some embodiments, the one or more frequencies can have the same amplitude. In some embodiments, the one or more frequencies can have a different amplitudes. Referring now to FIG. 9, an exemplary plot 902 shows an alternating electric field, having two stacked frequencies as a function of time. The data presented in FIG.

Figure 10:
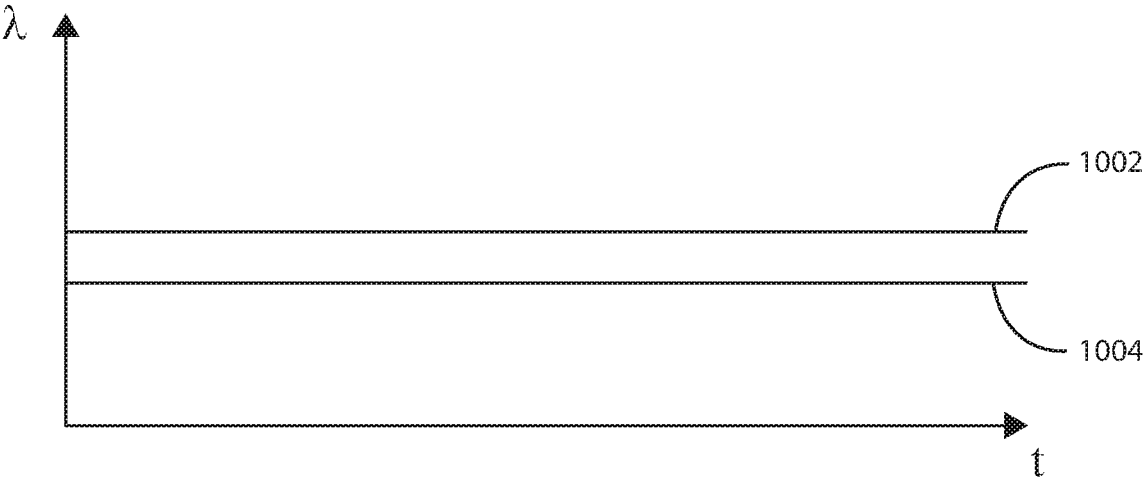
FIG. 10 is a plot of an exemplary therapy parameter in accordance with various embodiments herein.

9 can be alternatively presented as in FIG. 10, which shows a first frequency 1002 and a second frequency 1004 as a function of time throughout the duration of the therapy. The first frequency 1002 and second frequency 1004 can be combined (stacked or superimposed on one another) in order to create a combined frequency pattern. In some embodiments, the control circuitry can be configured to deliver an electric field having a waveform representing the superposition of at least two frequencies at least 10%, 20%, 30%, 40%, 50%, 60%, 70%, 100%, 300% or 1000% different from one another.

Stepped Frequencies

Figure 11:
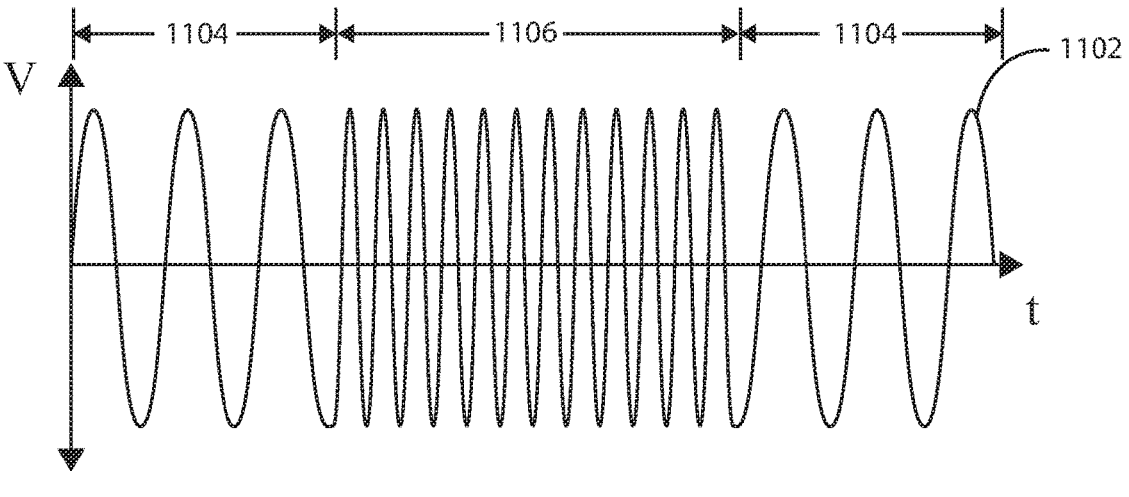
FIG. 11 is a plot of an exemplary therapy parameter in accordance with various embodiments herein.
Figure 12:
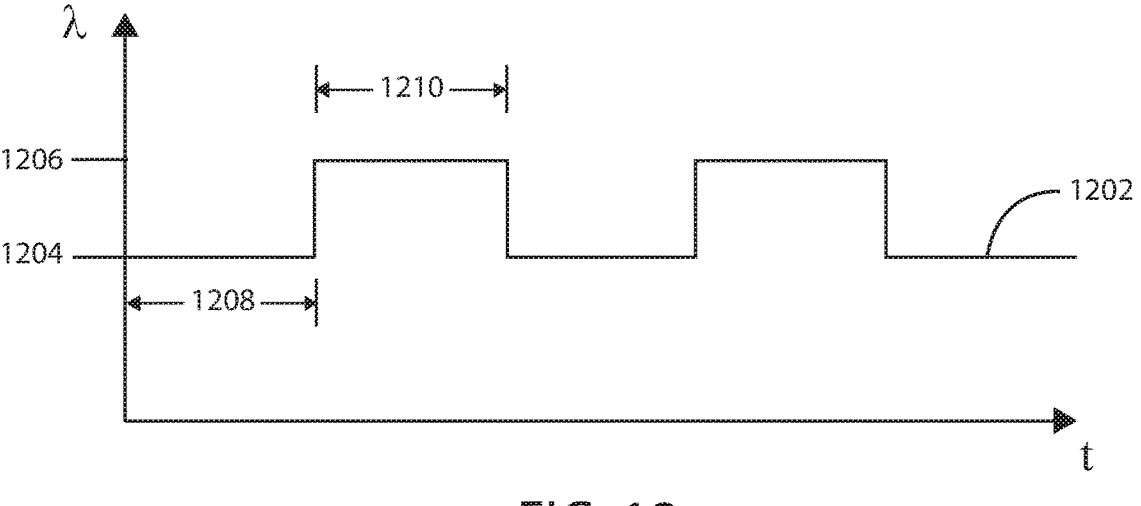
FIG. 12 is a plot of an exemplary therapy parameter in accordance with various embodiments herein.

In some embodiments, a therapeutic parameter set can include applying an electric field to the site of a cancerous tumor by stepping through one or more frequencies throughout the duration of the therapy. Referring now to FIG. 11, exemplary plot 1102 shows an alternating electric field, where the frequency changes from a first frequency 1104 to a second frequency 1106 and back to the first frequency 1104 as a function of time. An additional example is shown in FIG. 12, where exemplary plot 1202 shows applying an electric field by stepping through a first frequency 1204 and second frequency 1206 as function of time.

The amount of time spent at any given frequency before stepping from one frequency to another frequency can be referred to as the dwell time. In some instances, a dwell time can be the time spent at any given frequency, and in other instances, a dwell time can be the time spent in an OFF time state where no electric field is generated. In some embodiments, the OFF times are defined by the voltage remaining at an electrical potential bias voltage, which could be 0V or another voltage. In some instances, the bias voltage can be from −5V to 5V. In other instances, the bias voltage can be 0V.

In some embodiments, stepping through the one or more frequencies can include a first predetermined dwell time at a first frequency. In other embodiments, stepping through one or more frequencies can also include a second predetermined dwell time at a second frequency. For example, exemplary plot 1202 shows a first dwell time 1208 at a first frequency 1204 and a second dwell time 1210 at a second frequency 1206. In some embodiments, the first predetermined dwell time can be in the range of 1 sec to 1 minute, 1 minute to 1 hour, or 1 hour to 10 hours. In some embodiments, the second predetermined dwell time can be in the range of 1 sec to 1 minute, 1 minute to 1 hour, or 1 hour to 10 hours. In some embodiments, the first and second predetermined dwell times can be the same. In some embodiments, the first and second predetermined dwell times can be different.

Programmable Electric Fields

In some embodiments, programmable electric fields can be used to apply one or more electric fields to the site of a cancerous tumor. In some examples, the programmable electric field can be implemented temporally. In other embodiments, the programmable electric field can be implemented spatially.

Figure 13:
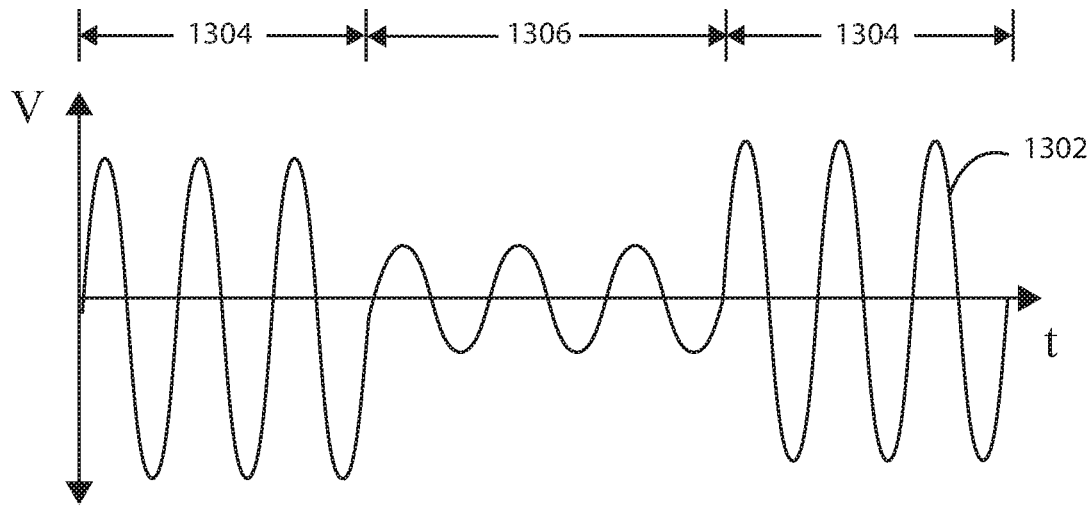
FIG. 13 is a plot of an exemplary therapy parameter in accordance with various embodiments herein.

Referring now to FIG. 13, exemplary plot 1302 shows an alternating electric field, where the electric field strength changes between a first electric field 1304 having an electric field strength $E_1$ to a second electric field 1306 having an electric field strength $E_2$, as a function of time. In some embodiments, the therapy can include alternating between one or more electric field strengths as a function of time. Without being bound by theory, it is believed that high electric field strengths are optimal for preventing cell division, however, sustained high electric field strengths can result in excessive tissue heating and potentially electroporation. By programming the electric field strength to alternate between a high electric field strength and a low electric field strength, the side effects can be minimized or eliminated altogether. Additionally, programming the electric field strength to alternate between a high electric field strength and a low electric field strength can provide the added benefit of reducing the energy requirement during the course of treatment, thus saving battery life over the lifetime of the medical device.

In some embodiments, the control circuitry 206 can be configured to generate high electric field strengths of greater than or equal to 10 V/cm. In some embodiments, the control circuitry 206 can be configured to alternate between generating electric field strengths of equal to or greater than 10 V/cm to generating electric field strengths of between 1 V/cm to 10 V/cm. In other embodiments, the control circuitry 206 can be configured to generating electric field strengths of between 3V/cm to 5 V/cm.

Figure 14:
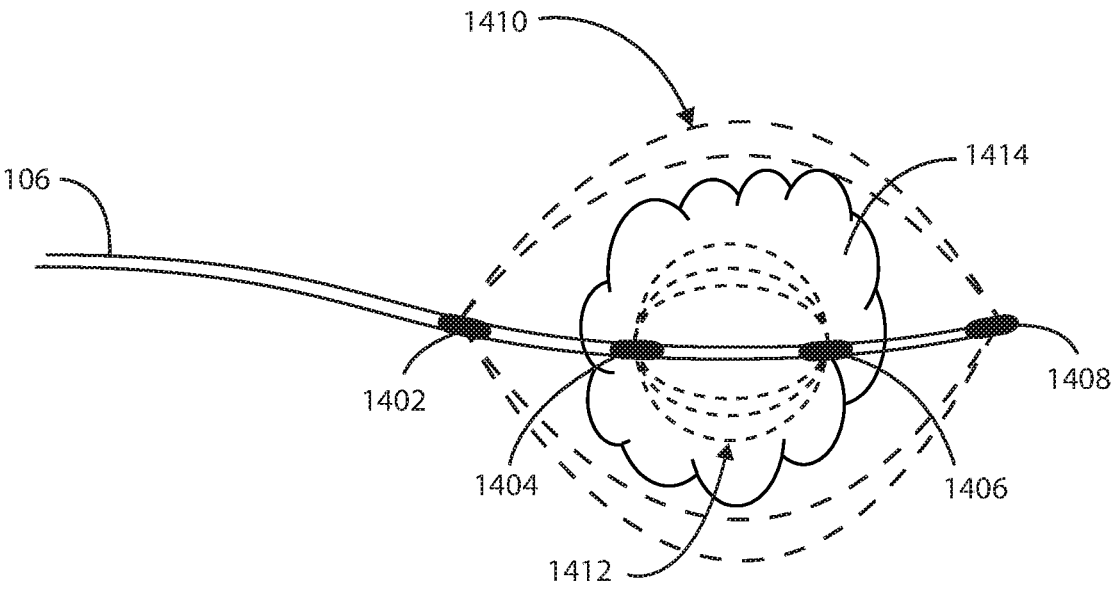
FIG. 14 is a schematic diagram of a lead in accordance with various embodiments herein.

Referring now to FIG. 14, a schematic diagram of a lead 106 implementing another example of a programmable electric field strength is shown in accordance with the embodiments herein. In some embodiments, spatially varying the one or more electric fields can include programming a first electric field strength between a first pair of electrodes and programming a second electric field strength between a second pair of electrodes. For example, lead 106 can include electrodes 1402, 1404, 1406, and 1408 disposed along its length. Electrodes 1402, 1404, 1406, and 1408 can generate a plurality of electric field vectors between one or more pairs of electrodes.

A first electric field 1410 having an electric field strength $E_1$ is shown disposed between electrodes 1402 and 1408 in the region of tumor 1414. Similarly, a second electric field 1412 strength $E_2$ is shown disposed between electrodes 1404 and 1406 in the region of tumor 1414. The first electric field 1410 and second electric field 1412 can be applied simultaneously or in an alternating, or stepped, fashion. Though only two electric fields having different electric field strengths are shown in FIG. 14, it will be appreciated that more than two electric fields having different or the same electric field strengths can be contemplated in accordance with the embodiments herein. Additionally, at least one electric field can be generated between any of electrodes 1402, 1404, 1406, or 1408 and the housing of the medical device (not shown). While FIG. 14 shows a substantially straight orientation for the lead 106, it will be appreciated that in many embodiments the lead may be implanted so as to be curved or otherwise bent at specific points in order to allow for greater spatial diversity between specific vectors as defined by electrode pairs.

It will be appreciated that various electric field vectors will be influenced by different impedances due to the local environment through which the electric field is propagated. Thus, in some embodiments, to achieve the same electric field strength between one or more separate pairs of electrodes, it may be necessary to generate a stronger electric field at a first pair of electrodes than at a second pair of electrodes to achieve the same electric field strength. For example, the electric field generated between a first pair of electrodes can be stronger than the electric field generated between a second pair of electrodes to achieve the same electric field strength.

Electric Field Strength Sweep

Figure 15:
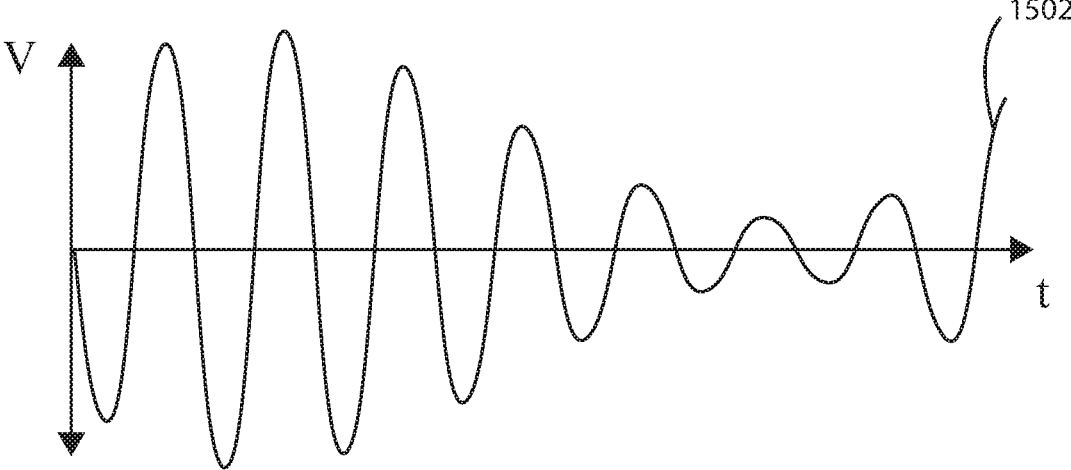
FIG. 15 is a plot of an exemplary therapy parameter in accordance with various embodiments herein.
Figure 16:
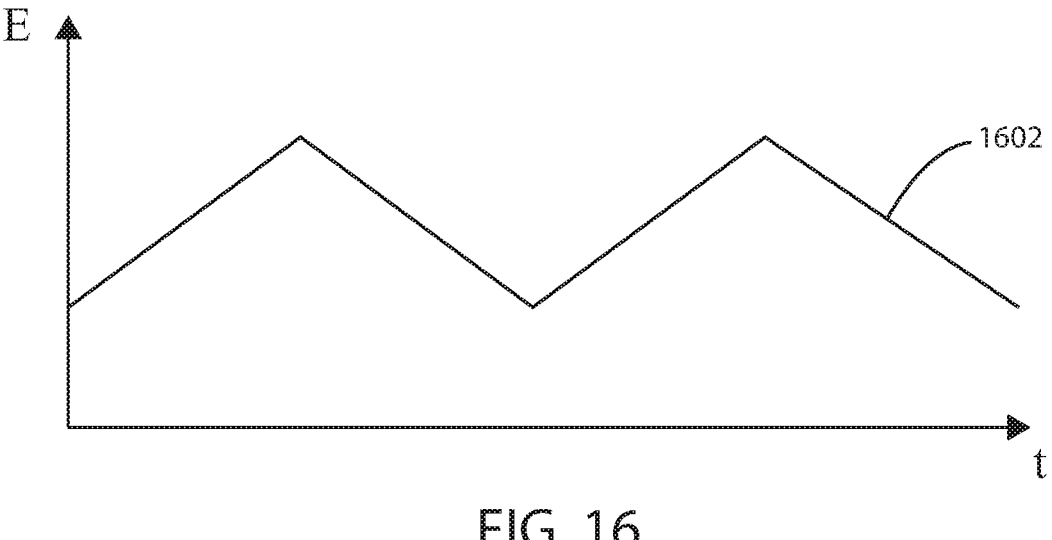
FIG. 16 is a plot of an exemplary therapy parameter in accordance with various embodiments herein.

In some embodiments, an electric field can be applied to the site of a cancerous tumor by sweeping through a range of electric field strengths. Referring now to FIG. 15, plot 1502 shows an alternating electric field, where the frequency of remains constant over time, but the electric field strength varies. Similarly, FIG. 16 shows the change in electric field strengths (E) as a function of time in exemplary plot 1602. In some embodiments, an electric field strength sweep can include sweeping from a minimum electric field strength up to a maximum electric field strength. In some embodiments, an electric field strength sweep can include sweeping from a minimum electric field strength up to a maximum electric field strength and sweeping from the maximum electric field strength down to the minimum electric field strength. In other embodiments, sweeping from a minimum electric field strength up to a maximum electric field strength and sweeping from the maximum electric field strength down to the minimum electric field strength can be repeated throughout the duration of the therapy.

Rotating Electric Field

In some embodiments, a therapeutic parameter set can be designed to create a rotating electric field about the site of a cancerous tumor. Without wishing to be bound by theory, it is believed that generating an electric field using multiple electrodes (for example across different vectors in sequence) can effectively create a rotating electric field that can induce a torsional and/or shear stress on the many polar proteins involved in mitosis. Disruptions in protein function essential to the mitotic process can halt cell division, induce protein degradation, and eventually lead to apoptosis.

Figure 17:
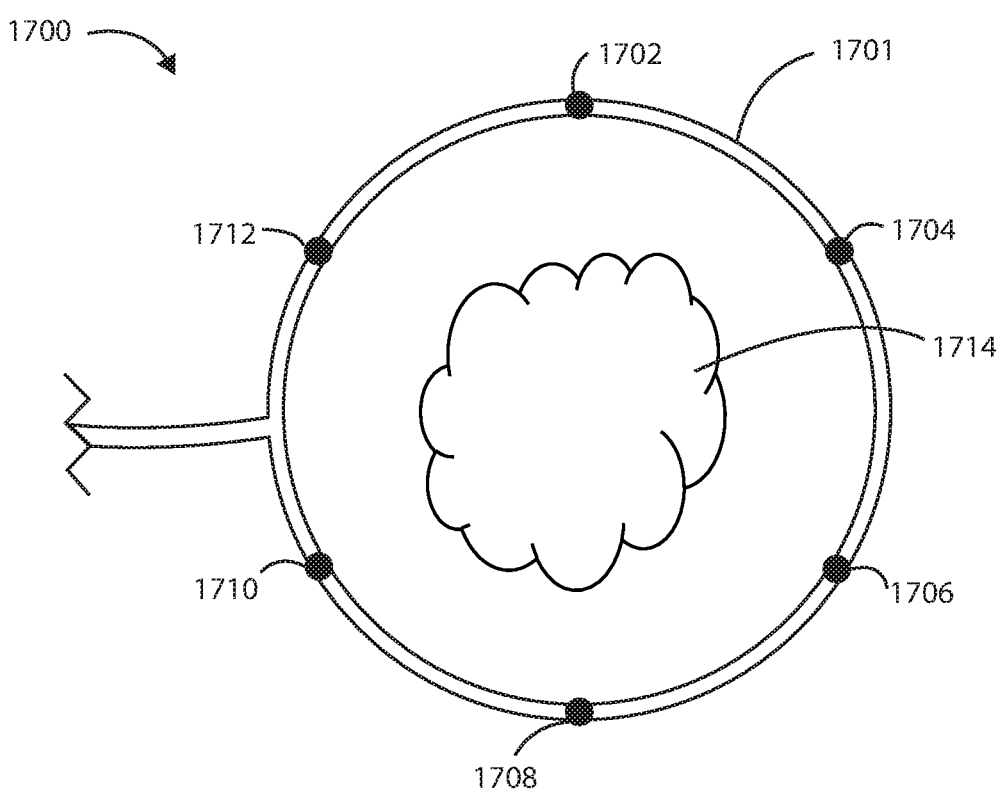
FIG. 17 is a schematic diagram of a lead in accordance with various embodiments herein.

Referring now to FIG. 17, a circular, multi-polar electrode system 1700 is shown in accordance with the embodiments herein. Circular lead 1701 can include circular electrodes 1702, 1704, 1706, 1908, 1710, and 1712 disposed around the circumference of the lead electrodes 1702, 1704, 1706, 1708, 1710, and 1712 disposed around the circumference of the lead can generated a plurality of electric field vectors disposed circumferentially about an axis of field rotation. Circular lead 1701 can be disposed in a region near or about a cancerous tumor 1714.

An effective rotating electric field can be generated by sequentially generating one or more electric fields at paired electrodes disposed about the circumference of circular lead 1701. In some embodiments, electrode pairs can be configured between electrodes disposed 180 degrees about the circumference of the circular lead. For example, in some embodiments, electrodes 1702 and 1708 can form a first electrode pair, electrodes 1704 and 1710 can form a second electrode pair, and electrodes 1706 and 1712 can form a third electrode pair. Each electrode pair can be sequentially stimulated in a clockwise or counter-clockwise fashion about the lead so that an electric field is created such that it can be effectively rotating about the site of the cancerous tumor 1714. In some embodiments, each electrode pair can be stimulated in a clockwise fashion for a first predetermined amount of time and then switched to a counter-clockwise fashion for a second predetermined amount of time. In some embodiments, rotating electric fields can also be generated relative to one master electrode paired to any or all of the one or more electrodes disposed about the circumference of the circular lead 1701. In some embodiments the circular lead can be a closed loop, as shown by circular lead 1701, and in other embodiments, the circular lead can be a semi-closed circular loop.

In some embodiments, the one or more electrode pairs are disposed about the circumference of the circular lead such that one or more electric fields can be generated about the lead. In other embodiments, sequentially generating an electric field at one or more electrode pairs can generate a three-dimensional electric field about the lead. In other embodiments, the effective rotating electric field can be created by sequentially generating more than one electric field between one master electrode paired to one or more additional electrodes disposed about the circumference of the lead.

It will be appreciated that while lead 1701 is shown in FIG. 17 as a closed, circular loop having multiple electrodes disposed thereon, many configurations of leads other than circular leads can be utilized to generate an effective rotating electric field. For example, one or more leads having multiple electrodes disposed thereon, such as the leads presented in FIG. 6, can be configured to generate an effective rotating electric field similar to that generated by circular lead 1701. In some examples, an effective rotating electric field can be generated by one or more leads having disposed along their length three or more electrodes comprising a plurality of electric field vectors. An effective rotating electric field can be generated by sequentially varying the electric field at one or more vectors disposed circumferentially about an axis of field rotation. The effective rotating electric field can also be generated by sequentially varying the electric field at one master electrode paired to one or more electrodes disposed circumferentially about an axis of field rotation. In some embodiments, sequentially varying the electric field at one or more vectors disposed circumferentially about an axis of field rotation can generate a three-dimensional electric field about the one or more vectors.

Figure 18:
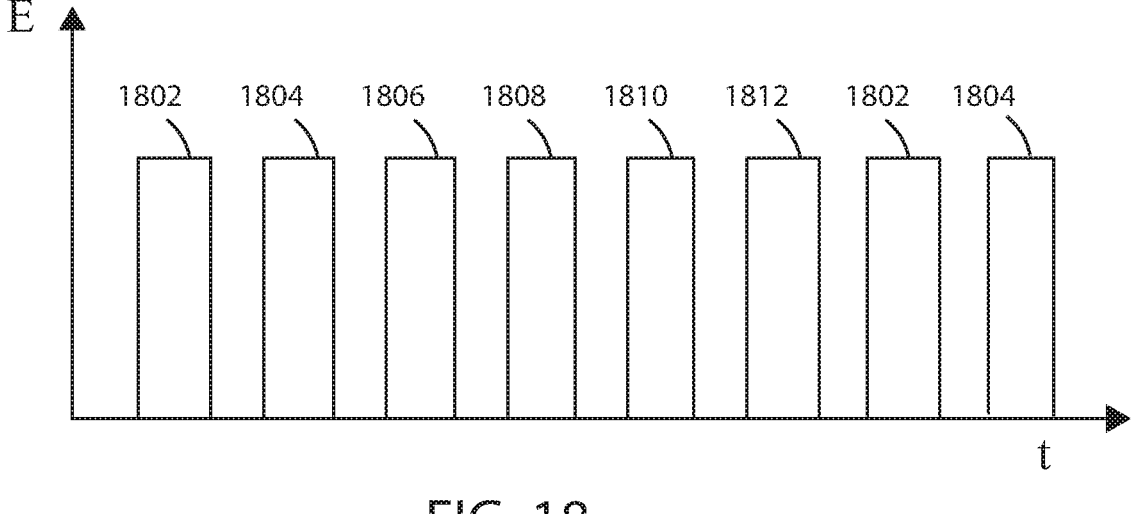
FIG. 18 is a plot of an exemplary therapy parameter in accordance with various embodiments herein.

Referring now to FIG. 18, a plot of electric field strength (E) as a function of time is shown. One or more electric field strengths 1802, 1804, 1806, 1808, 1810, and 1812 can correlate with one or more pairs of electrodes selected from the group of electrodes 1702, 1704, 1706, 1708, 1710, and 1712, respectively, as presented in FIG. 17. In some embodiments, the electric field strengths 1802, 1804, 1806, 1808, 1810, and 1812 can have the same amplitude. In other embodiments, the electric field strengths 1802, 1804, 1806, 1808, 1810, and 1812 can have the different amplitudes. As discussed with respect to FIG. 17, an effective rotating electric field can be generated by sequentially generating one or more electric fields between one or more pairs of electrodes disposed about the circumference of circular lead repeatedly throughout the duration of therapy. In some embodiments, the one or more pairs of electrodes can be disposed on one or more straight, curved, or biased leads positioned at, near, or through the site of a cancerous tumor such that the electrode pairs are disposed circumferentially about an axis of field rotation.

Voltage Mode and Current Control Mode

In some embodiments, the therapeutic parameter sets can include a voltage control mode or a current control mode. Electric field strength can be affected by the type of cancerous tumor, the location of the cancerous tumor within the body, and the size of the cancerous tumor, amongst other environmental conditions. Without intending to be bound by theory, it is understood that as an electric field is generated from one point to another at the site of a tumor, the local environment can exhibit a natural resistance (impedance) against that applied electric field.

Electric impedance can change throughout a course any given therapy. To address possibly changing electrical impedance, various control modes can be used in order to provide a desired electric field strength at the site of a cancerous tumor. Control modes herein can include both current and voltage control modes.

A current-based control mode can involve modulating the current provided by the medical device in order to generate an electric field of a desired strength at the site of treatment (such as at the site of a cancerous tumor). For example, in some embodiments, the current-based control mode can include generating an electric field across one or more vectors at a constant current and then assessing the electric field strength at the site of a tumor or another site using a sensing electrode or another type of electrical contact. Then the electric field strength can be adjusted account for any changes due to impedance, such that a constant electric field strength is maintained for the duration of therapy. The electric field can also be adjusted as desired by a clinician in order to optimize the therapy. In some embodiments, the control circuitry can be configured to record the electric field strength and one or more other parameters, such as the voltage, current, and/or impedance, into memory at any given time throughout the duration of the therapy.

A voltage-based control mode can involve modulating the voltage provided by the medical device in order to result in an electric field of a desired strength at the site of treatment (such as at the site of a cancerous tumor). For example, in some embodiments, the voltage-based control mode can include generating an electric field across one or more vectors and then assessing the electric field strength at the site of a tumor or another site using a sensing electrode or another type of electrical contact. Then the electric field strength can be adjusted accordingly to account for any changes due to impedance, such that a constant electric field strength is maintained for the duration of therapy. The electric field can also be adjusted as desired by a clinician in order to optimize the therapy. In some embodiments, the control circuitry can be configured to record the electric field strength and one or more other parameters, such as the voltage, current, and/or impedance, into memory at any given time throughout the duration of the therapy.

Duty Cycles

In some embodiments, it will be advantageous to implement therapeutic parameter sets using one or more duty cycles. Without intending to be bound by theory, it is believed that not all cells in a cancerous tumor will be undergoing mitosis at the same time. Implementing a duty cycle can generate one or more electric fields at the site of a heterogeneous population of mitotic cells such that multiple cell populations can be targeted during the course of a therapy. Additionally, the duty cycle mode can reduce drain on battery supply by eliminating the need to generate an electric field at the site of the cancerous tumor 100% of the time. Implementing various duty cycle modes can also lessen the effects of potential side effects caused by prolonged electric field exposure at the tumor site, such as tissue heating.

Figure 19:
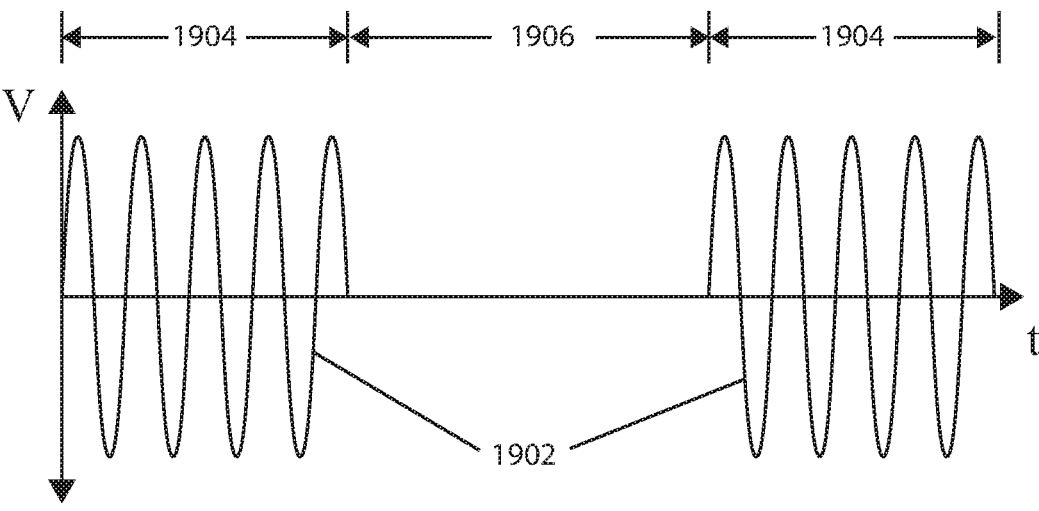
FIG. 19 is a plot of an exemplary therapy parameter in accordance with various embodiments herein.
Figure 20:
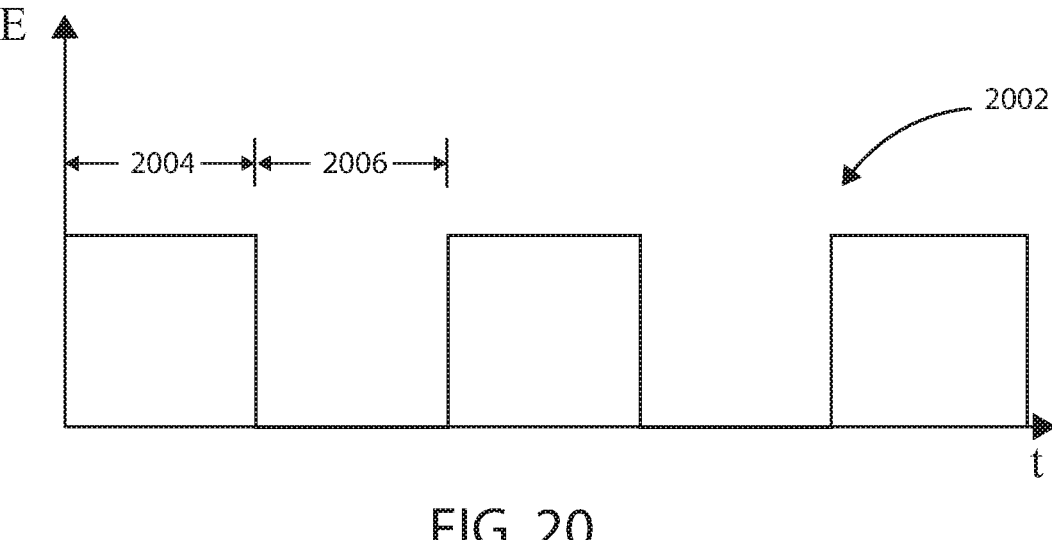
FIG. 20 is a plot of an exemplary therapy parameter in accordance with various embodiments herein.

Referring now to FIG. 19, plot 1902 shows an example of implementing a duty cycle in accordance with the embodiments herein. Plot 1902 shows a duty cycle having an ON time 1904 and an OFF time 1906 while sweeping through various frequencies as a function of time. Plot 1902 can cycle between ON time 2104 and OFF time 1906 throughout the duration of the therapy. Similarly, bar graph 2002 of FIG. 20 shows a duty cycle having an ON time 2004 and an OFF time 2006, with a constant applied electric field strength as a function of time. In some embodiments, implementing one or more duty cycles can include generating an electric field at a constant frequency for a predetermined ON time, followed by a predetermined OFF time. In some embodiments, implementing one or more duty cycles can include generating an electric field at a constant electric field strength for a predetermined ON time, followed by a predetermined OFF time.

In some embodiments, the predetermined ON or OFF times can be selected from microseconds, seconds, minutes or hours. In some embodiments, the predetermined ON time can be 10 microseconds, 500 microseconds, 1 millisecond, 10 milliseconds, 100 milliseconds, 500 milliseconds, 1 second, 5 seconds, 30 seconds, 1 minute, 10 minutes, 30 minutes, 1 hour, 2 hours, 4 hours, 8 hours, 12 hours, 16 hours, 18 hours, 20 hours, 22 hours, or 23 hours, or within a range wherein any of the preceding amounts of time can serve as the upper or lower bound of the range. In some embodiments, the predetermined OFF time can be 10 microseconds, 500 microseconds, 1 millisecond, 10 milliseconds, 100 milliseconds, 500 milliseconds, 1 second, 5 seconds, 30 seconds, 1 minute, 10 minutes, 30 minutes, 1 hour, 2 hours, 4 hours, 8 hours, 12 hours, 16 hours, 18 hours, 20 hours, 22 hours, or 23 hours, or within a range wherein any of the preceding amounts of time can serve as the upper or lower bound of the range.

Pulse-Width Modulation

Figure 21:
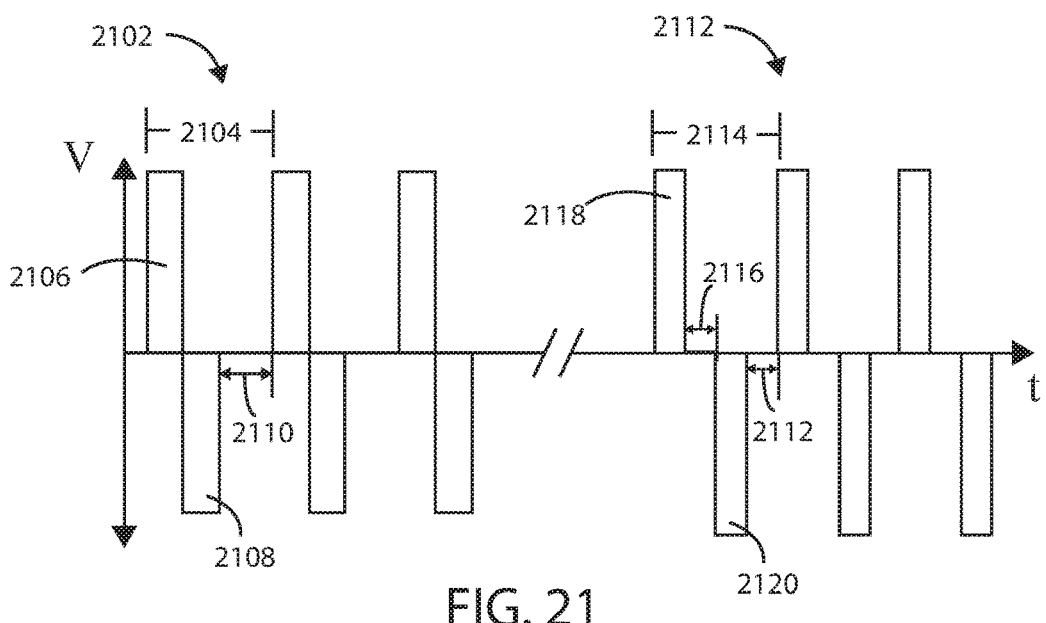
FIG. 21 is a plot of an exemplary therapy parameter in accordance with various embodiments herein.
Figure 22:
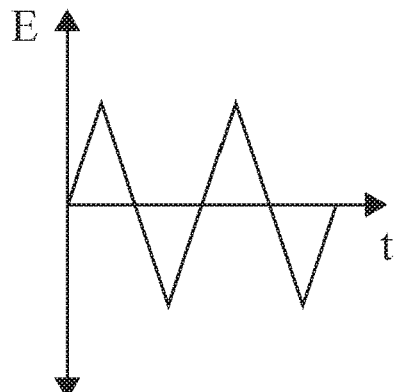
FIG. 22 is a schematic view of an exemplary waveform in accordance with various embodiments herein.
Figure 23:
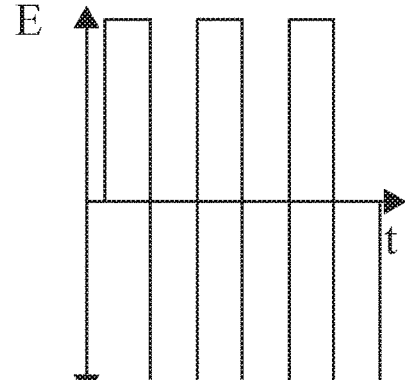
FIG. 23 is a schematic view of an exemplary waveform in accordance with various embodiments herein.
Figure 24:
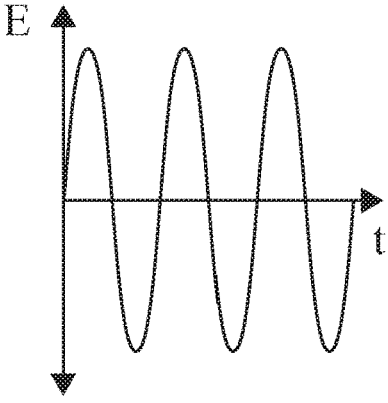
FIG. 24 is a schematic view of an exemplary waveform in accordance with various embodiments herein.

The electric field can be manipulated by modulating the pulse width as a function of time when applied to a site of a cancerous tumor. Many pulse-width modifications can be contemplated in accordance with the embodiments herein. In some embodiments, the control circuitry can be configured to generate one or more electric fields having an electrical waveform alternating between positive pulses and negative pulses, where the electrical waveform can include one or more OFF times between at least some adjacent positive and negative pulses. FIG. 21 shows two possible pulse-width modifications that can be configured to allow for using a faster frequency that requires less energy per period of applied electric field. For example, the pulse width modification shown in plot 2102 includes a period 2104 that has no OFF time between an applied positive pulse 2106 and an applied negative pulse 2108, but includes an OFF time 2110 as a part of the overall period of the applied electric field. The ON time, or dwell time of positive pulse 2106 and negative pulse 2108 can be adjusted in many ways to shorten or lengthen the predetermined OFF time 2110 per period 2104. Thus, the when higher frequencies are used to generate an electric field during therapy, the overall ON time can be reduce, thus reducing the overall energy input required throughout the duration of treatment. Similarly, another example is shown in plot 2112, which includes a period 2114 that has an alternating field having a first OFF time 2116 programmed between an applied positive pulse 2118 and an applied negative pulse 2120. This can be followed by a second OFF time 2122 as a part of the overall period of the applied electric field.

In some embodiments, the OFF times are defined by an electrical potential bias voltage. In some instances, the bias voltage can be from −5V to 5V. In other instances, the bias voltage can be 0V.

Electrical Waveforms

Figure 25:
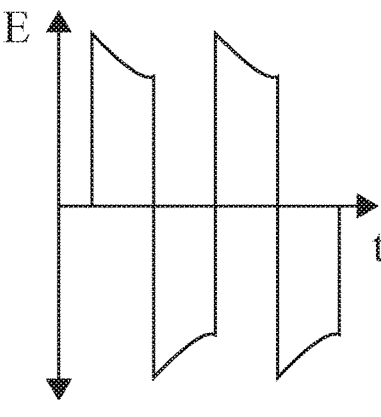
FIG. 25 is a schematic view of an exemplary waveform in accordance with various embodiments herein.

The electric fields described herein can be generated from many different electrical waveforms. Each unique electrical waveform can have a specific period, frequency, and amplitude. The electrical waveforms can be selected from one or more of a triangular waveform, square waveform, a sinusoidal waveform, a capacitive decay waveform, or the like. FIGS. 22-25 show examples of a triangular waveform (FIG. 22), a square waveform (FIG. 23), a sinusoidal waveform (FIG. 24), or a capacitive decay waveform (FIG. 25). The waveform shape and directionality can be modulated throughout the duration of treatment to provide therapy using one or more frequencies, durations, and strengths. For example, in some embodiments, the therapy parameter can be programmed to begin as a sinusoidal waveform and transition into a square waveform. Similarly, the therapy parameter can be programmed to begin as a square waveform and transition into a capacitor-decaying waveform. Any combinations of the waveforms discussed herein are suitable for use in the therapy parameter types described.

In some embodiments, the control circuitry can be configured to generate unique electrical waveforms by manipulating the directionality and sequence of one or more pulses. Additionally, dwell times can be included before, between, or after any number of pulses within a given period to manipulate the ON and OFF times for any given pulse sequence. In some embodiments, the unique electrical waveform can be biphasic. In some examples, the biphasic electrical waveform can include one positive pulse followed by one negative pulse, as shown in FIGS. 22-25, and 27. In some examples, the biphasic electrical waveform can include two positive pulses followed by two negative pulses, as shown in FIG. 26. A biphasic electrical waveform can also include two negative pulses followed by two positive pulses as shown in FIG. 30.

In other non-limiting examples, the unique electrical waveform can be triphasic and include three positive pulses followed by three negative pulses (FIG. 28) or three negative pulses followed by three positive pulses (FIG. 29). In some embodiments, the electrical waveform can be tetraphasic include four positive pulses followed by four negative pulses, or four negative pulses followed by four positive pulses.

In some embodiments, the control circuitry can be configured to generate one or more electric fields having an electrical waveform including a sequence of positive pulses, negative pulses, and OFF times. The electrical waveform can include at least one of two positive pulses separated by an OFF time but not a negative phase, or two negative pulses separated by an OFF time but not a positive phase. The positive pulses and negative pulses can be relative to a bias voltage. The OFF times can be defined by an electrical potential equal to the bias voltage. The bias voltage can fall anywhere within the range from −5 V to 5 V. In some embodiments, the bias voltage can be 0 V.

High Frequency Pulse or High Field Strength Pulse

In certain embodiments, the therapy parameter sets described herein can be programmed to apply a single high frequency pulse or a single high electric field strength at programmed intervals throughout the duration of the applied therapy. In some embodiments, the use of single pulses at high frequency (>1 MHz) or at high electric field strength (>1000V/cm)) can be used alone, or in conjunction with one or more of the therapy parameters described herein. To avoid or lessen side effects associated with generating electric fields at high frequencies or high field strengths for prolonged periods, the single high frequency pulse or a single high electric field strength can be implemented at intervals within the millisecond or second timescales.

Methods

Various methods can be performed utilizing the medical devices and the steps described with respect to the various therapy parameters described herein.

In some embodiments, methods for providing treatment for a cancerous tumor are included in accordance with the embodiments herein. The methods can include generating electric fields using a medical device. The medical device can include an electric field generating circuit configured to generate one or more electric fields and control circuitry in communication with the electric field generating circuit. The control circuitry can be configured to control the generation of one or more electric fields by the electric field generating circuit. The method can also include using the control circuitry to direct the electric field generating circuit to generate one or more electric fields at one or more frequencies selected from a range of between 10 kHz to 1 MHz to a cancerous tumor located within a bodily tissue. In some embodiments, the medical device can be implanted entirely within the body, and in other embodiments, the medical device can be partially implanted within the body. The electric field applied to the site of the cancerous tumor can be effective to prevent and disrupt cellular mitosis in a cancerous cell.

In some embodiments, the medical device can also include one or more leads in electrical communication with the electric field generating circuit. The one or more leads can each include one or more electrodes in electrical communication with the electric field generating circuit. The medical device used in accordance with the methods herein can include a housing in which the electric field generating circuit and the control circuitry are disposed, where the housing can includes a portion that is in electrical communication with the electric field generating circuit to serve as an electrode.

In some examples, it may be desirable to periodically generate an electric field using frequencies greater than 1 MHz. In other examples, it may be desirable to generate an electric field by sweeping through one or more frequencies. Sweeping through one or more frequencies can include sweeping from a minimum frequency up to a maximum frequency and sweeping from the maximum frequency down to the minimum frequency. Sweeping through one or more frequencies can also include a cycle of sweeping from a minimum frequency up to a maximum frequency and sweeping from the maximum frequency down to the minimum frequency, such that the cycle is repeated throughout the duration of the therapy.

In some embodiments, the method can include generating an electric field by stacking one or more frequencies simultaneously. The one or more frequencies can have an identical amplitude or the one or more frequencies can have a different amplitude.

The methods herein can also include generating an electric field by stepping through one or more frequencies. Stepping through one or more frequencies can include a first predetermined dwell time at a first frequency before stepping to a second frequency. Stepping through one or more frequencies can also include a second predetermined dwell time at a second frequency before stepping back to the first frequency. In some embodiments, the first predetermined dwell time and second predetermined dwell time can be in the range of 1 sec to 1 minute, 1 minute to 1 hour, or 1 hour to 10 hours. In some embodiments, the first and second predetermined dwell times are the same. In other embodiments, the first and second predetermined dwell times are different.

Methods described herein can further include programming the electric field strength. In some embodiments, the methods can include generating an electric field correlating to one or more programmable electric field strengths. The one or more programmable electric field strengths can be selected from a range of electric field strengths between 0.25 V/cm to 1000 V/cm. In some examples, generating an electric field using one or more programmable electric field strengths can include varying the one or more electric field strengths as a function of time. In other embodiments, generating an electric field using one or more programmable electric field strengths can include spatially varying one or more electric field strengths about the site of the cancerous tumor. Spatially varying the one or more electric field strengths can include programming a first electric field between a first pair of electrodes and programming a second electric field between a second pair of electrodes. In some embodiments, programming the electric field strength can include programming the electric field strength to a value equal to or greater than 10 V/cm. In some embodiments, programming the electric field strength can include programming the electric field strength to a value within a range from 1 V/cm to 10 V/cm. In some embodiments, programming the electric field strength can include programming the electric field strength to a value within a range from 3 V/cm to 5 V/cm. In other embodiments, programming the electric field strength can include programming the electric field strengths to alternate between generating one of greater than or equal to 1000 V/cm and generating electric field strengths of between 0.25 V/cm to 500 V/cm.

Some methods can include generating an electric field by sweeping through one or more electric field strengths. Sweeping through one or more electric field strengths can include sweeping from a minimum electric field strength up to a maximum electric field strength and sweeping from the maximum electric field strength down to the minimum electric field strength. Sweeping from a minimum electric field strength up to a maximum electric field strength and sweeping from the maximum electric field strength down to the minimum electric field strength can be repeated throughout the duration of the therapy. In some embodiments, when sweeping through one or more electric field strengths, the one or more electric fields strengths cane be selected from a range of electric field strengths between 0.25 V/cm to 1000 V/cm.

Some methods can involve generating an electric field by using a voltage control mode or a current control mode as described above.

In some embodiments, the method can include generating an electric field by implementing one or more duty cycles throughout the duration of therapy. Without being bound by theory, it is believed that a duty cycle can be understood as the ratio of time a circuit is on compared to the ration of time the circuit is off. A duty cycle can be expresses as a percentage of ON time in one full duty cycle. One full duty cycle includes the ON time and the OFF time for one full period of the applied waveform. Implementing one or more duty cycles can include generating an electric field at a constant frequency for a predetermined ON time, followed by a predetermined OFF time. In other embodiments, implementing one or more duty cycles can include generating an electric field at a constant electric field strength for a predetermined ON time, followed by a predetermined OFF time. The ON time and OFF time can be adjusted according to the particular duty cycle to be implemented. Thus, the predetermined ON time can selected from a range between 4 hours to 18 hours, and the predetermined OFF time is selected from a range between 6 hours to 20 hours In some embodiments, the methods can include generating an electric field by delivering one or more pulses. Each pulse can generate a unique electrical waveform. Each unique electrical waveform can include a period, frequency, and amplitude. In some embodiments, the electrical waveform is biphasic. The biphasic electrical waveform can include one positive pulse followed by one negative pulse. In other embodiments, the biphasic electrical waveform can include two positive pulses followed by two negative pulses. Though the embodiments herein only include one or two positive pulses followed by one or two negative pulses, any combination of positive and negative pulses are suitable for use with the methods herein. In some embodiments, the unique electrical waveform can be selected from one or more of a triangular waveform, a square waveform, a sinusoidal waveform, or a capacitive decay waveform.

In some embodiments, a medical device capable of generating a rotating electric field is contemplated. The medical device capable of generating a rotating electric field can include an electric field generating circuit configured to generate one or more electric fields and control circuitry in communication with the electric field generating circuit. The control circuitry can be configured to control the generation of one or more electric fields from the electric field generating circuit. The medical device can also include one or more leads in electrical communication with the electric field generating circuit. The control circuitry can cause the electric field generating circuit to deliver an electric field at frequencies selected from a range of between 10 kHz to 1 MHz to a cancerous tumor located within a bodily tissue. In some embodiments, the medical device can be implanted entirely within the body, and in other embodiments the medical device can be partially implanted within the body. The one or more leads of the medical device can include one or more circular leads, or the one or more leads can include three or more electrodes comprising a plurality of electric field vectors disposed circumferentially about an axis of field rotation.

Medical devices having one or more circular leads can have one or more electrodes disposed about the circumference of the one or more circular leads. The one or more electrodes can include one or more electrode pairs disposed about the circumference of the one or more circular leads to sequentially generating an electric field at the one or more electrode pairs. In some embodiments, sequentially generating an electric field at the one or more electrode pairs can generate a three-dimensional electric field about the one or more circular leads.

Medical devices having one or more leads comprising three or more electrodes comprising a plurality of electric field vectors disposed circumferentially about an axis of field rotation can be also be configured to create an effective rotating electric field via the plurality of electric field vectors disposed circumferentially about an axis of field rotation. In some embodiments, the effective rotating electric field is generated by sequentially varying the electric field at the one or more vectors disposed circumferentially about an axis of field rotation. The effective rotating electric field can be generated by sequentially varying the electric field at one master electrode paired to one or more electrodes disposed circumferentially about the axis of field rotation. Sequentially varying the electric field at one or more vectors disposed circumferentially about an axis of field rotation can generate a three-dimensional electric field about the one or more vectors.

Leads and Electrodes

The leads described herein can be placed into the body near the site of a cancerous tumor using a number of techniques. Placement of one or more leads can include using techniques such as transvascular placement, tunneling into the subcutaneous space, and/or surgical placement. In some embodiments, the placement of one or more leads can include placement via one or more natural body orifices. The leads can be placed adjacent to or within a cancerous tumor. In some embodiments, multiple leads can be used near to or far from the cancerous tumor.

In some embodiments one or more leads described herein can be placed in the subcutaneous space. Electrodes on leads placed in the subcutaneous space can be used as the primary near-field generating electrode or as a far-field field generating electrode. In some embodiments, electrodes on leads placed in the subcutaneous space can be used as the primary near-field generating electrode or as a far-field field generating electrode in conjunction with the housing of a medical device. Likewise, one or more leads can be placed transvascularly to act as far-field field generating electrodes in conjunction with an electrode at or near the site of the cancerous tumor or in conjunction with the housing of a medical device.

The leads and electrodes described herein can include additional functional and structural features. In some embodiments, the leads can include those that are compatible with imaging and treatment techniques, including but not limited to MRI (magnetic resonance imaging), X-ray imaging, deep brain stimulation techniques, and/or radiation therapy. In some embodiments, the leads can include one or more conductor cores made from conducting materials. The conductor cores can be formed from conducting materials including metals and/or other conducting materials. Metals can include, but are not limited to, palladium, platinum, silver, gold, copper, aluminum, various alloys including stainless steel, nickel-cobalt alloys such as MP35N® and the like. In some embodiments, the conductor core can be a multifilar coil, including but not limited to a bifilar coil, a trifilar coil, and a quadfilar coil.

In some embodiments, electrodes can be disposed along the length of one or more leads as described herein. Suitable materials for use in the electrodes described herein can include metals such as palladium, to minimize coupling and artifact generation in magnetic fields. In some embodiments, electrodes can be made from other metals and/or other conducting materials. Metals can include, but are not limited to, palladium, platinum, platinum alloys such as platinum-iridium alloy, gold, copper, tantalum, titanium, various alloys including stainless steel, and the like. In some embodiments, electrodes can be in the form of wound coils that can provide an added benefit of increased surface area without compromising flexibility of the electrodes. In some embodiments, the implantable device housing can serve as an electrode.

The leads described herein can also include one or more electrodes disposed along the length of the lead. The leads can include two or more electrodes disposed along the length of the lead. In some embodiments, the electrodes can be tip electrodes found at the distal end of the lead. In other embodiments, the electrodes can be ring electrodes found along the lead but not at the tip of the lead. In some embodiments, the electrodes can be coil electrodes. In some embodiments, a ring or tip electrode can be positioned in or adjacent to a tumor or cancerous tissue and a coil electrode can be positioned farther from the tumor or cancerous tissue in order to help provide spatial diversity to the generated electric fields. In some embodiments, one or more electrodes can have a length along the lengthwise axis (e.g., proximal to distal axis) of about 0.5, 1, 1.5, 2, 3, 4, 5, 7.5, 10, 15, 20, 30, 40, 50, 75, 100 mm or more. In some embodiments, one or more of the electrodes can have a length falling within a range wherein any of the foregoing distances can serve as the upper or lower bound of the range, provided that the upper bound is greater than the lower bound.

The leads can be unipolar, bipolar, or multipolar. In some embodiments, a unipolar lead can include a lead that generates an electric field between one electrode and the housing of the medical device. In some embodiments, a bipolar lead can include a lead that can generate and electric field between two electrodes disposed along the lead, or between both electrodes and the housing of the medical device. In some embodiments, a multipolar lead can include a lead that can generate an electric field between the more than two electrodes disposed along the lead, between more than two electrodes and the housing of the medical device, or any number of combinations of configurations of electrodes and the housing of the medical device.

The electrodes suitable for use here can be made of conductive polymers such as carbon filled silicone, polyacetylene, polypyrrole, polyaniline, polytiophene, polyfuran, polyisoprene, polybutadiene, polyparaphenylene, and the like. In other embodiments, the electrodes can be insulated. In some embodiments, the insulation surrounding and electrode can include microporous insulators to prevent cellular apposition, yet still allow for current flow. Microporous insulators can be made from a number of the insulating materials described herein, including but not limited to polytetrafluoroethylene (ePTFE), polyethylene-co-tetrafluoroethene (ETFE), polyurethanes, silicones, poly(p-xylylene) polymers such as Parylene polymers, polyether block amides such as PEBAX®, nylons, or derivatives thereof. In some embodiments, the electrodes can be coated with various materials, including but not limited to hydrogels or fractal coatings such as iridium oxide, titanium oxide, tantalum pentoxide, other metal oxides, poly(p-xylylene) polymers such as Parylene, and the like.

A number of lead fixation techniques and configurations can be used in accordance with the embodiments herein. Some non-limiting examples of lead fixation techniques can include biocompatible glue fixation, talon fixation, helix coil fixation, passive centering of the lead in the vascular system, tine fixation within the localized vascular system, spiral bias fixation within the localized vascular system, compression fixation, suture sleeve fixation, and the like. In some examples, the leads embodied herein can be placed within the vascular system surrounding or adjacent to the site of the cancerous tumor. In other embodiments, the leads embodied herein can be place surgically at or within or surrounding the site of the cancerous tumor.

The leads suitable for use herein can also include one or more open lumens that run the entire longitudinal length of, or a select portion of the longitudinal length of the lead. In some embodiments, the open lumen can include an integrated biopsy apparatus suitable for obtaining biopsy samples from a cancerous tumor site on a periodic basis to monitor disease progression and/or regression. Leads having an open lumen can also be configured to include an integrated drug delivery lumen that can deliver one or more drugs, such as steroids or chemotherapy agents, to the site of the tumor in a single bolus or periodically via a metered pump. The leads can include one or more portals disposed along the length of the lead to provide an outlet for drug delivery at or near the site of a cancerous tumor.

In some embodiments a portion of the lead or the entire lead can include a drug eluting coating. In some embodiments, the drug eluting coating can include an anti-inflammatory agent, such as a steroid. In some embodiments, the steroid can be dexamethasone. In other embodiments, the drug eluting coating can include a chemotherapy agent. In some embodiments, the chemotherapy agent can include a taxane or derivatives thereof, including but not limited to paclitaxel, docetaxel, and the like. In other embodiments, the drug eluting coating can be configured to release additional classes of chemotherapy agents, including, but not limited to alkylating agents, plant alkaloids such as vinca alkaloids, cytotoxic antibiotics, topoisomerase inhibitors, and the like.

In some embodiments, the drug eluting coating can be configured to release the drug from the coating in a time-release fashion.

The leads herein can adopt a number of shapes or configurations. In some embodiments, the leads can be linear and in other embodiments the leads can be circular. A circular lead may be a completely closed loop or it may be a semi-closed loop. In some embodiments, the lead can include a bendable core that can allow the lead to be shaped into many configurations, including but not limited to a U shape, an S shape, a spiral shape, a half circle, an oval, and the like.

In yet other examples, the leads suitable for use herein can include fluorimetric or magnetic markers that can assist the clinician in precise placement at or near the site of a cancerous tumor. The leads can also include integrated pH sensors for detecting the change in the pH at or near the cancerous tumor or other chemical sensors suitable for analyzing the concentration of a chemical analyte of interest.

Electric Field Generators

The medical devices embodied herein can include electric field generators particularly suited for therapeutic and diagnostic techniques used during the course of treatment for a cancerous tumor. In some embodiments, the electric field generators suitable for use herein can include those that have been treated by radiation hardening to make the components resistant to the damaging effects of radiation therapy treatments often prescribed as a main line treatment for cancerous tumors. Electric field generators can include components such as those described in reference to FIGS. 3 and 5 above.

Electric field generators embodied herein can be programmed with any number of therapeutic parameter sets as described. The electric field generators can be programmed prior to implant, or they can be programmed by a clinician using an external computation device such as a programmer, a home-based unit, and/or a mobile unit (e.g. a cellular phone, personal computer, smart phone, tablet computer, and the like). In some embodiments, therapy parameters can be delivered to the electric field generator via a telemetry circuit. In some embodiments, the electric field generator can include a recharge circuit communicatively coupled to a receiver coil to facilitate transcutaneous recharging of the medical device. In some embodiments, the electric field generator can communicate wirelessly between the receiver coil and an external charging device.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A medical device comprising:
an electric field generating circuit configured to generate two or more electric fields; and
control circuitry in communication with the electric field generating circuit, the control circuitry configured to control delivery of the two or more electric fields from the electric field generating circuit; and
one or more leads in electrical communication with the electric field generating circuit, wherein each of the one or more leads comprise four or more electrodes disposed along a length of each of the one or more leads;
wherein the control circuitry causes the electric field generating circuit to generate the two or more electric fields at frequencies selected from a range of between 10 kHz to 1 MHz at a site of a cancerous tumor located within a bodily tissue, wherein the two or more electric fields are effective to prevent and/or disrupt cellular mitosis in a cancerous cell;
wherein the two or more electric fields are delivered along more than one vector between at least two pairs of the four or more electrodes surrounding the cancerous tumor, wherein a first pair of the four or more electrodes is positioned between a second pair of the four or more electrodes such that the second pair of the four or more electrodes has a broader electric field reach than the first pair of the four or more electrodes; and
wherein the control circuitry is further configured to generate the two or more electric fields having an electrical waveform alternating between positive pulses and negative pulses, the waveform including one or more OFF time periods between at least some adjacent positive and negative pulses, wherein the positive pulses and negative pulses are relative to a bias voltage between −5 V and 5 V and the one or more OFF time periods is defined by an electrical potential equal to the bias voltage.

2. The medical device of claim 1, wherein the electric field generating circuit generates the two or more electric fields at frequencies selected from a range of between 100 kHz to 300 kHz.

3. The medical device of claim 1, the medical device further comprising an electric field sensing circuit, the electric field sensing circuit comprising a first sensing electrode and a second sensing electrode, wherein the electric field sensing circuit is configured to measure an electrical potential difference between the first sensing electrode and the second sensing electrode.

4. The medical device of claim 1, wherein the control circuitry is further configured to generate the two or more electric fields with a waveform representing a superposition of at least two frequencies at least 10% different from one another.

5. The medical device of claim 1, wherein the control circuitry is further configured to generate the two or more electric fields by stepping through one or more frequencies, wherein stepping through the one or more frequencies includes a first predetermined dwell time at a first frequency, and a second predetermined dwell time at a second frequency.

6. The medical device of claim 1, wherein the control circuitry is further configured to generate the two or more electric fields having one or more programmable electric field strengths, wherein the one or more programmable electric field strengths are selected from a range of electric field strengths from 3 V/cm to 5 V/cm.

7. The medical device of claim 1, wherein the control circuitry is further configured to generate the two or more electric fields having two or more programmable electric field strengths and to alternate between generating electric field strengths of greater than 10 V/cm to generating electric field strengths of between 2 V/cm to 10 V/cm.

8. The medical device of claim 1, wherein the control circuitry is further configured to generate the two or more electric fields by sweeping through one or more electric fields comprising one or more electric field strengths, wherein sweeping through the two or more electric fields comprising one or more electric field strengths includes sweeping from a first electric field strength up to a second electric field strength and sweeping from the second electric field strength down to the first electric field strength, wherein the second electric field strength is higher than the first electric field strength.

9. The medical device of claim 1, wherein the control circuitry is further configured to generate the two or more electric fields by using a voltage control mode, the voltage control mode including modulating voltage in order to produce a desired electric field strength, or by using a current control mode, the current control mode including modulating current in order to produce a desired electric field strength, wherein the control circuit is further configured to adjust the current to maintain a substantially constant electric field strength.

\* \* \* \* \*